United States Patent
MacDonald et al.

(10) Patent No.: US 7,964,602 B2
(45) Date of Patent: Jun. 21, 2011

(54) BIARYL COMPOUNDS USEFUL AS AGONISTS OF THE GPR38 RECEPTOR

(75) Inventors: Gregor James MacDonald, Harlow (GB); Darren Jason Mitchell, Harlow (GB); Mervyn Thompson, Harlow (GB); Susan Marie Westaway, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 206 days.

(21) Appl. No.: 12/096,104

(22) PCT Filed: Dec. 1, 2006

(86) PCT No.: PCT/EP2006/011734
§ 371 (c)(1),
(2), (4) Date: Jun. 4, 2008

(87) PCT Pub. No.: WO2007/065669
PCT Pub. Date: Jun. 14, 2007

(65) Prior Publication Data
US 2008/0306083 A1   Dec. 11, 2008

(30) Foreign Application Priority Data

Dec. 5, 2005 (GB) .................................. 0524814.1

(51) Int. Cl.
*A61K 31/496* (2006.01)
*C07D 401/14* (2006.01)
*C07D 409/14* (2006.01)
*C07D 417/14* (2006.01)
(52) U.S. Cl. ........... 514/253.01; 514/253.09; 514/253.1; 514/253.11; 514/253.12; 544/364
(58) Field of Classification Search .................. None
See application file for complete search history.

(56) References Cited

U.S. PATENT DOCUMENTS

| 6,200,978 | B1 | 3/2001 | Maw et al. |
| 7,262,195 | B2 | 8/2007 | Li et al. ..................... 514/252.06 |
| 7,700,599 | B2 | 4/2010 | Thompson et al. ...... 514/253.12 |
| 7,767,692 | B2 | 8/2010 | Jasserand et al. ............. 514/315 |
| 2003/0203922 | A1 | 10/2003 | Patel et al. ............... 514/266.21 |
| 2004/0152732 | A1 | 8/2004 | Jasserand et al. |
| 2005/0065156 | A1 | 3/2005 | Li et al. ......................... 514/248 |
| 2005/0080116 | A1 | 4/2005 | Li et al. ......................... 514/354 |
| 2007/0225292 | A1 | 9/2007 | Amin et al. ................ 514/252.1 |
| 2008/0027065 | A1 | 1/2008 | Mitchell et al. .......... 514/252.11 |
| 2009/0054456 | A1 | 2/2009 | Johnson et al. .......... 514/253.13 |
| 2009/0131453 | A1 | 5/2009 | Seal et al. ................ 514/255.01 |
| 2009/0192160 | A1 | 7/2009 | Mitchell et al. ............ 514/235.8 |
| 2010/0256364 | A1 | 10/2010 | Mitchell et al. ............... 544/121 |

FOREIGN PATENT DOCUMENTS

| JP | 09249620 | 9/1997 |
| WO | WO02/092592 A1 | 11/2002 |
| WO | WO 2008/000729 A1 | 1/2008 |

OTHER PUBLICATIONS

Ozaki et al. Pharmacology, vol. 79, p. 223-235 (2007).*
ter Beek et al. Inflamm. Bowel Dis. vol. 14, p. 612-619 (2008).*
*Chemical Abstracts Service*, Caplus, XP002452868, 2005:612264 (2005).
Filewrapper for U.S. Appl. No. 11/995,416 filed Jun. 9, 2008.
Filewrapper for U.S. Appl. No. 12/304,539 filed Dec. 12, 2008.
Filewrapper for U.S. Appl. No. 11/768,339 filed Jun. 26, 2007.
Filewrapper for U.S. Appl. No. 12/417,176 filed Apr. 2, 2009.
Filewrapper for U.S. Appl. No. 12/744,367 filed May 24, 2010.

* cited by examiner

*Primary Examiner* — Emily Bernhardt
(74) *Attorney, Agent, or Firm* — Kathryn L. Sieburth; John Lemanowicz

(57) ABSTRACT

The present invention relates to novel biaryl derivatives such as compounds of formula (I), which have activity as agonists of the GPR38 receptor and the use of such compounds or pharmaceutical compositions thereof in the treatment of gastrointestinal disorders.

11 Claims, No Drawings

BIARYL COMPOUNDS USEFUL AS AGONISTS OF THE GPR38 RECEPTOR

The present invention relates to novel biaryl derivatives having pharmaceutical activity, processes for their preparation, pharmaceutical compositions containing them and to their use in the treatment of various disorders.

GPR38 is a 7-transmembrane, G-protein coupled receptor, with high affinity for the peptide motilin [Feighner et al., Science 1999, 284, 2184], suggesting that endogenous motilin exerts all or most of its activity via this receptor.

Motilin is a 22 amino acid peptide found in large amounts within endocrine-like cells of the gastrointestinal tract, and especially in the duodenum-jejunum areas. During fasting, the peptide is known to be associated with the onset of Phase III migrating complex activity within the stomach [Boivin et al., Dig. Dis. Sci. 1992, 37, 1562], suggesting a role in the mechanisms of this prokinetic activity. Motilin is also released from the gut during feeding, sham feeding, gastric distension or by oral or intravenous nutrient application [Christofides et al., Gut 1979, 20, 102; Bormans et al., Scand. J. Gastroenterol. 1987, 22, 781], suggesting additional roles for this peptide in the modulation of motility patterns during feeding.

In animals or in man, motilin has long been known to increase gastrointestinal motility, and promote gastric emptying and intestinal propulsion in an anal direction, during both fasting and fed conditions. This activity is thought to be primarily due to a facilitation of at least the cholinergic excitatory function of the gut [Van Assche et al., Eur. J. Pharmacol. 1997, 337, 267], perhaps also involving the activation of the vagus nerve [Mathis & Malbert, Am. J. Physiol. 1998, 274, G80]. In addition, higher concentrations of motilin directly evoke a small contraction of the muscle [Van Assche et al., Eur. J. Pharmacol. 1997, 337, 267].

The antibiotic erythromycin was shown to mimic the gastrointestinal activity of motilin, in addition to its previously-described antibiotic properties [see Peeters, in *Problems of the Gastrointestinal Tract in Anaesthesia* Ed., Herbert M K et al. Springer-Verlag, Berlin, Heidelberg 1999, pp 39-51]. More recently, erythromycin has been shown to activate the GPR38 receptor, confirming its ability to mimic the function of motilin [Carreras et al., Analyt. Biochem. 2002, 300, 146]. In addition, the availability of this non-peptide motilin receptor agonist has allowed at least some clinical studies to be undertaken in order to examine the clinical potential of motilin receptor agonists. These studies have consistently demonstrated an ability to increase gastric emptying in various conditions associated with gastroparesis, such as functional dyspepsia and diabetic gastroparesis. Further, erythromycin has been shown to increase lower esophageal sphincter pressure in man, which together with the increase in gastric emptying, suggests a role in the treatment of gastroesophageal reflux disease (GERD). Finally, erythromycin has been used to promote intestinal propulsive activity, finding clinical utility in the treatment of pseudo-obstruction and in conditions with impaired colonic motility [Peeters, in *Problems of the Gastrointestinal Tract in Anaesthesia* Ed., Herbert M K et al. Springer-Verlag, Berlin, Heidelberg 1999, pp 39-51].

Consequently it is expected that agonists at the GPR38 receptor will mimic the activity of motilin and find clinical utility in the treatment of gastrointestinal disorders associated with hypomotility, especially the functional bowel disorders such as GERD, functional dyspepsia (FD) and irritable bowel syndrome (IBS). The compounds will also be useful for the treatment of other GI conditions where the cause is known and in which GI motility is reduced. Such conditions include constipation, caused by various diseases such as those associated with neuropathy, and/or by the administration of other drugs, intestinal pseudo-obstruction, paralytic ileus following surgery or some other manipulation, gastric stasis or hypomotility caused by various diseases such as diabetes and/or by the administration of other drugs. Interestingly, the ability of motilin or erythromycin to activate the vagus nerve, the association of this nerve with changes in feeding behaviour [eg. Furness et al., Auton. Neurosci. 2001, 92, 28] and the chromosomal location of GPR38 [based on Ensembl: 13q21.1 (58.46-59.46 Mb)] within the markers (D13S257-13q14.11 to D13S258 at 13q21.33) of a locus associated with obesity [Feitosa et al, Am. J. Hum. Genet. 2002, 70, 72] also suggests that agonists active at the GPR38 receptor will, in addition to promoting gastrointestinal motility, facilitate eating behaviours in at least those patients in which some degree of appetite suppression or cachexia is present. Such activity indicates that agonists at this receptor will find clinical utility in the treatment of symptoms associated with—for example—the treatment of cancer or by the presence of the cancer itself.

In addition to the ability of motilin receptor agonists to promote gastrointestinal motility, the association of motilin gene polymorphism with Crohn's disease [Annese et al., Dig. Dis. Sci. 1998, 43, 715-710] and the changes in motilin receptor density during colitis [Depoortere et al., Neurogastroenterol. Motil. 2001, 13, 55] suggests a utility for agonists at the motilin receptor for the treatment of inflammatory bowel conditions in general.

Finally, GPR38 is also found in regions outside the gastrointestinal tract. These areas include the pituitary, adipose tissue, urinary bladder and certain areas of the brain. The former suggests clinical utility in the promotion of pituitary function, such as the release of growth hormone secretagogues, the presence within adipose tissue again suggests a role in the control of body weight, and the presence within the urinary bladder suggests a role for agonists at this receptor in the treatment of incontinence. The presence of GPR38 within the brain supports the gastrointestinal and feeding utilities already mentioned, but in addition, suggests an involvement of the receptor in a greater spectrum of vagal-hypothalamic functions.

Patents WO9410185, EP838469, WO9823629, DE19805822, and U.S. Pat. No. 6,165,985 claim erythromycin derivatives targeting GPR38 for use in disorders relating to gastrointestinal motility. Patents WO9921846, WO0185694, WO0168620, WO168621, and WO0168622 disclose a series of small molecule antagonists of the GPR38 receptor. Patents JP07138284 and EP807639 disclose peptide agonists. JP09249620 and WO02092592 disclose a series of small molecule agonists.

A structurally novel class of compounds has now been found which are partial or full agonists at the GPR38 receptor.

In a first aspect, the present invention therefore provides a compound of formula (I), or a pharmaceutically acceptable salt or solvate thereof,

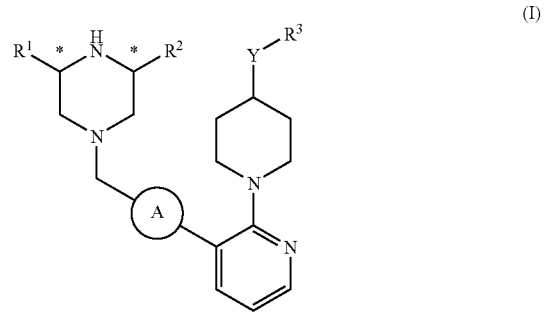

wherein

A is selected from a 5 or 6 membered heteroaryl ring and an N-linked 5 or 6 membered heterocyclic ring; which ring is optionally substituted with 1, 2 or 3 groups independently selected from halogen, $C_{(1-4)}$ alkyl and $C_{(1-4)}$ alkoxy;

$R^1$ and $R^2$ are independently selected from H or $C_{(1-4)}$ alkyl;

Y is selected from NH, O and $CH_2$;

$R^3$ is selected from optionally substituted phenyl and optionally substituted 5 or 6 membered heteroaryl;

and when $R^3$ is substituted, it may have 1, 2 or 3 substituents, each independently selected from halogen, $C_{(1-4)}$alkyl, $C_{(1-4)}$ alkoxy, $C_{(3-7)}$cycloalkyl, hydroxy, trifluoromethoxy, trifluoromethyl, nitro, cyano, phenyl, $NH_2$, $NHR^4$, $NR^4R^5$, $NHCOR^4$, $NHSO_2R^4$, $C(O)CF_3$, $C(O)C_{(1-4)}$alkyl, $C(O)C_{(3-7)}$ cycloalkyl, $C(O)OC_{(1-4)}$alkyl, $C(O)OC_{(3-7)}$cycloalkyl, $OC(O)C_{(1-4)}$alkyl, $OC(O)C_{(3-7)}$cycloalkyl, $CONH_2$, $CONHR^4$, $CONR^4R^5$, $SOR^5$, $SO_2R^5$, $OSO_2R^5$, $OSO_2CF_3$, $SO_2NH_2$, $SO_2NHR^4$ and $SO_2NR^4R^5$;

where $R^4$ and $R^5$ may be the same or different and are independently selected from $C_{(1-4)}$ alkyl, phenyl optionally substituted with halogen, and 5 or 6 membered heteroaryl optionally substituted with halogen.

The term "alkyl" as a group or part of a group e.g. alkoxy or hydroxyalkyl refers to a straight or branched alkyl group in all isomeric forms. The term "$C_{(1-4)}$ alkyl" refers to an alkyl group, as defined above, containing at least 1, and at most 4 carbon atoms Examples of such alkyl groups include methyl, ethyl, propyl, iso-propyl, n-butyl, iso-butyl, sec-butyl, or tert-butyl, Examples of such alkoxy groups include methoxy, ethoxy, propoxy, iso-propoxy, butoxy, iso-butoxy, sec-butoxy and tert-butoxy.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "5 or 6 membered heteroaryl" represents a 5 or 6 membered aromatic ring which comprises one or more heteroatoms. When the term heteroaryl represents a 5 membered group it contains, for example, a heteroatom selected from O, N or S and it may optionally contain a further 1, 2 or 3 nitrogen atoms. When heteroaryl represents a 6-membered group it contains, for example, from 1 to 3 nitrogen atoms. Examples of such 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

The term "5 or 6 membered heterocyclic ring" refers to a heterocyclic ring having 5 or 6 atoms in total. A heterocyclic ring may, for example, be at least partially saturated. A heterocyclic ring may be saturated. When A is a 5 or 6 membered N-linked heterocyclic ring, it contains a Nitrogen atom and it may optionally contain one or two further heteroatoms selected from nitrogen, oxygen or sulfur. When the further heteroatom is nitrogen then this may be present as NH or an N-substituted derivative thereof e.g. N-alkyl, N-acyl. When the further heteroatom is sulphur this may be present as the SO, $SO_2$. Examples of such 5 or 6 membered heterocyclic rings include pyrrolidinyl, piperidinyl, piperazinyl, morpholinyl, thiomorpholinyl, imidazolidinyl, pyrazolidinyl, oxazolidinyl, isothiazolidinyl, thiazolidinyl, thiazinanyl, and pyranyl.

In one embodiment of the invention, both $R^1$ and $R^2$ are methyl. In an alternative embodiment of the invention, both $R^1$ and $R^2$ are hydrogen. In a further alternative embodiment, $R^1$ is hydrogen and $R^2$ is methyl.

In one embodiment, Y is NH or O. For example, Y may be NH.

Exemplary substituents for group $R^3$ include halogen, cyano, $C_{(1-4)}$alkyl, $C_{(1-4)}$alkoxy, $C_{(3-7)}$cycloalkyl, trifluoromethoxy and trifluoromethyl, for example halogen.

In one embodiment of the invention, $R^3$ is phenyl substituted by 1 substituent which is selected from halogen, cyano or $C_{(1-4)}$alkoxy, for example halogen, for example fluoro.

In a further embodiment of the invention, $R^3$ is phenyl substituted by 2 substituents, one of which is may be halogen, for example fluoro, and one of which is may be $C_{(1-4)}$alkoxy.

In a further embodiment of the invention, A is selected from pyrazolyl, thiazolyl, furanyl, thienyl and pyridyl.

In a further embodiment in which A is an N-linked 5 or 6 membered heterocyclic ring, optionally substituted with 1, 2 or 3 groups independently selected from halogen, $C_{(1-4)}$ alkyl or $C_{(1-4)}$ alkoxy, the N-linked ring is N-linked to the neighbouring pyridine group.

In certain of the compounds of formula (I), dependent upon the nature of the substituent there are chiral carbon atoms, such as the carbon atom marked with an "*", and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses. Preferred compounds of formula (I) wherein $R^1$ and $R^2$ are other than hydrogen e.g. methyl are those wherein the piperazine C* carbons have the 3R,5S-configuration.

Certain of the compounds herein can exist in various tautomeric forms and it is to be understood that the invention encompasses all such tautomeric forms.

Exemplary compounds of the invention are:

1-[3-(3-{[(3R,5S)-3,5-Dimethyl-1-piperazinyl]methyl}-1H-pyrazol-1-yl)-2-pyridinyl]-N-(4-fluorophenyl)-4-piperidinamine (E1)

1-[3-(3-{[(3R,5S)-3,5-dimethyl-1-piperazinyl]methyl}-1H-pyrazol-1-yl)-2-pyridinyl]-N-(3-fluorophenyl)-4-piperidinamine (E2)

1-[3-(3-{[(3R,5S)-3,5-dimethyl-1-piperazinyl]methyl}-1H-pyrazol-1-yl)-2-pyridinyl]-N-(2-fluorophenyl)-4-piperidinamine (E3)

1-[3-(5-{[(3R,5S)-3,5-Dimethyl-1-piperazinyl]methyl}-1,3-thiazol-2-yl)-2-pyridinyl]-N-(4-fluorophenyl)-4-piperidinamine (E4)

1-[3-(5-{[(3R,5S)-3,5-dimethyl-1-piperazinyl]methyl}-2-furanyl)-2-pyridinyl]-N-(4-fluorophenyl)-4-piperidinamine (E5)

1-[3-(5-{[(3R,5S)-3,5-Dimethyl-1-piperazinyl]methyl}-2-thienyl)-2-pyridinyl]-N-(4-fluorophenyl)-4-piperidinamine (E6)

1-[3-(4-{[(3R,5S)-3,5-Dimethyl-1-piperazinyl]methyl}-1,3-thiazol-2-yl)-2-pyridinyl]-N-(4-fluorophenyl)-4-piperidinamine dihydrochloride (E7)

1-[3-(4-{[(3R,5S)-3,5-dimethyl-1-piperazinyl]methyl}-1,3-thiazol-2-yl)-2-pyridinyl]-N-(3-fluorophenyl)-4-piperidinamine (E8)

1-[3-(4-{[(3R,5S)-3,5-dimethyl-1-piperazinyl]methyl}-1,3-thiazol-2-yl)-2-pyridinyl]-N-(2-fluorophenyl)-4-piperidinamine (E9)

1-(5-{[(3R,5S)-3,5-Dimethyl-1-piperazinyl]methyl}-2,3'-bipyridin-2'-yl)-N-(4-fluorophenyl)-4-piperidinamine (E10)

N-(4-Fluorophenyl)-1-[3-(3-{[(3S)-3-methyl-1-piperazinyl]
methyl}-1H-pyrazol-1-yl)-2-pyridinyl]-4-piperidinamine
(E11)

(3R,5S)-1-{[1-(2-{4-[(4-Fluorophenyl)oxy]-1-piperidinyl}-
3-pyridinyl)-1H-pyrazol-3-yl]methyl}-3,5-dimethylpip-
erazine (E12)

(3R,5S)-1-{[1-(2-{4-[(2-Fluorophenyl)oxy]-1-piperidinyl}-
3-pyridinyl)-1H-pyrazol-3-yl]methyl}-3,5-dimethylpip-
erazine (E13)

(3R,5S)-1-{[1-(2-{4-[(3-Fluorophenyl)oxy]-1-piperidinyl}-
3-pyridinyl)-1H-pyrazol-3-yl]methyl}-3,5-dimethylpip-
erazine (E14)

(3S)-1-{[1-(2-{4-[(3-Fluorophenyl)oxy]-1-piperidinyl}-3-
pyridinyl)-1H-pyrazol-3-yl]methyl}-3-methylpiperazine
(E15)

(3S)-1-{[1-(2-{4-[4-Fluorophenyl)oxy]-1-piperidinyl}-3-
pyridinyl)-1H-pyrazol-3-yl]methyl}-3-methylpiperazine
monohydrochloride (E16)

1-(5-{[(3R,5S)-3,5-Dimethyl-1-piperazinyl]methyl}-2,3'-
bipyridin-2'-yl)-N-(3-fluorophenyl)-4-piperidinamine
(E17)

N-(4-Fluorophenyl)-1-(5-{[(3S)-3-methyl-1-piperazinyl]
methyl}-2,3'-bipyridin-2'-yl)-4-piperidinamine (E18)

N-(4-Fluorophenyl)-1-[5-(1-piperazinylmethyl)-2,3'-bipyri-
din-2'-yl]-4-piperidinamine hydrochloride (E19)

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

In a further aspect, this invention provides processes for the preparation of a compound of formula (I) or a pharmaceutically acceptable salt or solvate thereof,

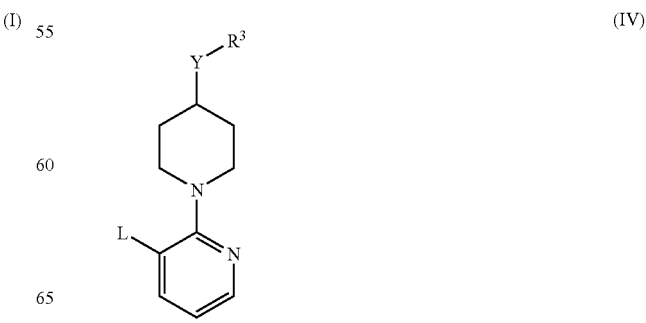

(I)

which process comprises reacting a compound of formula (II),

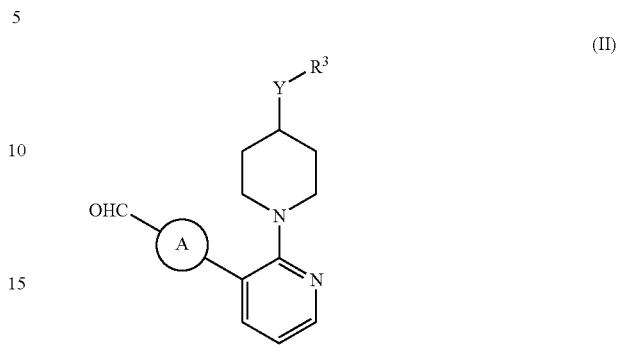

(II)

wherein A, Y and $R^3$ are as defined in relation to formula (I), with an appropriately substituted piperazine (III),

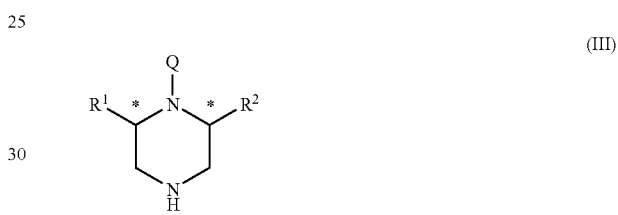

(III)

wherein $R^1$ and $R^2$ are as defined in relation to formula (I) and Q is hydrogen or a suitable nitrogen protecting group such as tert-butyloxycarbonyl (BOC) or trifluoroacetyl, in reaction conditions suitable for a reductive alkylation, for example in the presence of a reducing agent such as sodium tri(acetoxy) borohydride in a suitable solvent such as dichloromethane or 1,2-dichloroethane.

And thereafter optionally carrying out one or more of the following reactions:

1. Converting one compound of formula (I) into another compound of formula (I);
2. Removing any protecting group;
3. Forming a suitable pharmaceutical acceptable salt or solvate of the compound so formed.

Compounds of formula (II) may be prepared by reacting a compound of formula (IV), (IV)

wherein Y and R³ are as defined in relation to formula (I) and L is a leaving group such as bromine, with a suitable (formyl-heteroaryl) boronic acid derivative (V),

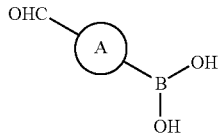

(V)

wherein A is as defined in relation to formula (I), in the presence of a suitable base such as sodium carbonate, in the presence of a suitable catalyst such as tetrakis(triphenylphosphine)palladium(0) or [1,1'-bis(diphenylphosphino)ferrocene] dichloropalladium(II), in a suitable solvent such as a (1:1) mixture of water and 1,2-dimethoxyethane.

Compounds of formula (IV) may be prepared by reacting a compound of formula (VI)

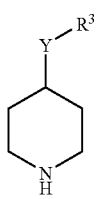

(VI)

wherein R³ and Y are as defined in relation to formula (I), with a compound of formula (VII),

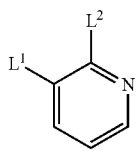

(VII)

wherein L¹ and L² are independently selected leaving groups, for example bromo or chloro, in the presence of a suitable base such as sodium carbonate or potassium carbonate, in the presence of a suitable solvent such as dimethylformamide.

Compounds of formula (VI) where Y=NH, may be prepared by a reductive alkylation reaction which involves reacting a suitable aniline derivative with a suitably protected piperidin-4-one, such as 1-(tert-butoxycarbonyl)piperidin-4-one, in the presence of a reducing agent such as sodium tri(acetoxy)borohydride, in a solvent such as 1,2-dichloroethane, followed by removal of the nitrogen protecting group by conventional techniques as described below.

Compounds of formula (VI), where Y=O, may be prepared by an alkylation reaction which involves reacting a suitable phenol derivative with a suitably protected 4-hydroxypiperidine, such as 1-(tert-butoxycarbonyl)-4-hydroxypiperidine in the presence of triphenylphosphine and diisopropylazodicarboxylate, in a solvent such as tetrahydrofuran, followed by removal of the nitrogen protecting group by conventional techniques as described below.

The present invention also provides a further process for the preparation of a compound of formula (I) wherein A is pyrazolyl, or a pharmaceutically acceptable salt or solvate thereof, which process comprises reacting a compound of formula (VIII),

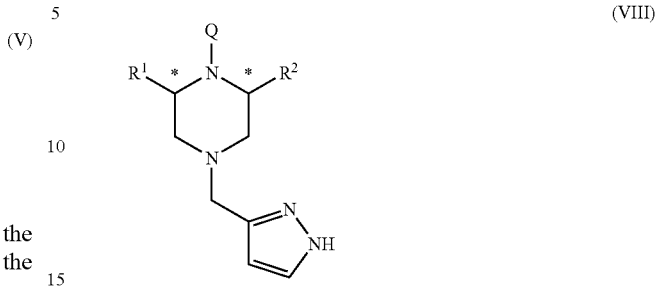

(VIII)

wherein R¹ and R² are defined in relation to formula (I) and Q is hydrogen or a suitable nitrogen protecting group such as benzyloxycarbonyl (CBZ), tert-butyloxycarbonyl (BOC), or trifluoroacetyl, with a compound of formula (IV),

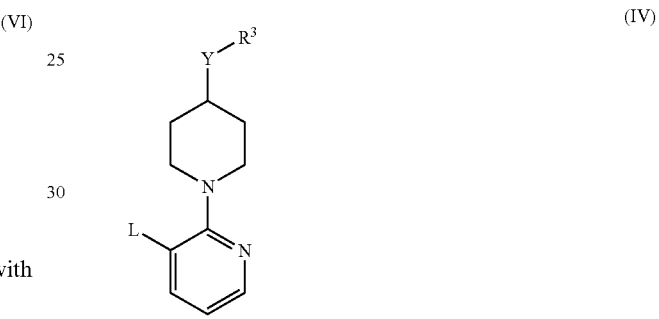

(IV)

wherein Y and R³ are as defined in relation to formula (I) above and L is a leaving group such as bromine, in the presence of a suitable base such as potassium carbonate, in the presence of a suitable catalyst such as a copper(I) source, for example copper(I) iodide, in a suitable solvent such as dimethyl sulfoxide, using methods similar to those described in S. V. Ley et al., Angew Chem. Int. Ed., 2003, 42, 5400.

And thereafter optionally carrying out one or more of the following reactions:

1. Converting one compound of formula (I) into another compound of formula (I);
2. Removing any protecting group;
3. Forming a suitable pharmaceutical acceptable salt or solvate of the compound so formed.

Compounds of formula (VIII) may be prepared by reacting a compound of formula (IX),

(IX)

wherein L is a suitable leaving group such as bromine and Z is a suitable protecting group such as tert-butyloxycarbonyl (BOC), with an appropriately substituted piperazine (III),

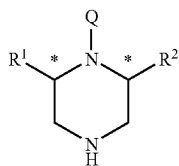

(III)

wherein R¹ and R² are as defined in relation to formula (I) and Q is hydrogen or a suitable nitrogen protecting group such as benzyloxycarbonyl (CBZ), tert-butyloxycarbonyl (BOC) or trifluoroacetyl, in the presence of a suitable base such as potassium carbonate, in a suitable solvent, for example dimethylformamide.

Compounds of formula (IX) wherein L is bromine, may be prepared by reacting a compound of formula (X),

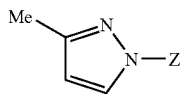

(X)

wherein Z is a suitable protecting group such as tert-butyloxycarbonyl (BOC), with a source of bromine such as N-bromosuccinimide, in the presence of a suitable radical initiator, for example benzoyl peroxide, in a suitable solvent such as carbon tetrachloride.

The present invention also provides a further process for the preparation of a compound of formula (I) or a pharmaceutically acceptable salt or solvate thereof, which process comprises reacting a compound of formula (XI),

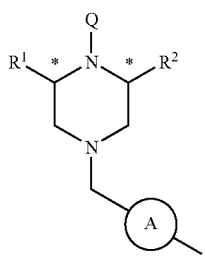

(XI)

wherein A, R¹ and R² are as defined in relation to formula (I), L is a leaving group such as chlorine or bromine and Q is hydrogen or a suitable nitrogen protecting group such as benzyloxycarbonyl (CBZ), tert-butyloxycarbonyl (BOC) or trifluoroacetyl, with a compound of formula (XII),

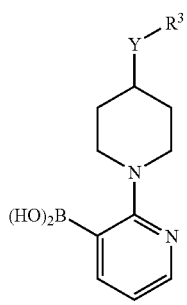

(XII)

wherein Y and R³ are as defined in relation to formula (I), in the presence of a suitable base such as sodium carbonate, in the presence of suitable catalyst such as tetrakis(triphenylphosphine)palladium (0), in a suitable solvent such as a (1:1) mixture of water and 1,2 dimethoxyethane.

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

The present invention also provides a still further process for the preparation of a compound of formula (I) or a pharmaceutically acceptable salt or solvate thereof, which process comprises reacting a compound of formula (XIII),

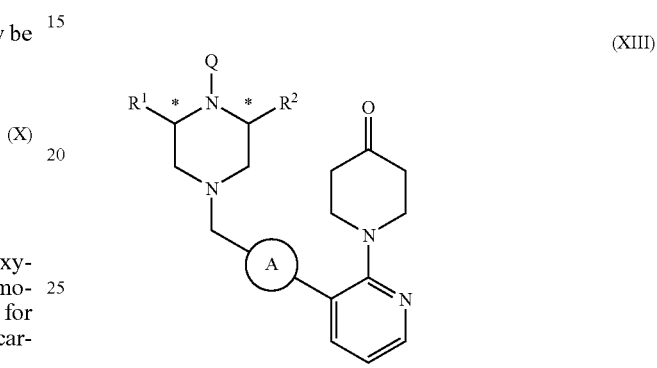

(XIII)

wherein A, R¹ and R² are as defined in relation to formula (I) and Q is hydrogen or a suitable nitrogen protecting group such as benzyloxycarbonyl (CBZ), tert-butyloxycarbonyl (BOC) or trifluoroacetyl, with a suitable aniline, under reaction conditions suitable for a reductive alkylation, for example in the presence of a reducing agent such as sodium tri(acetoxy)borohydride or sodium cyanoborohydride, in the presence of an acid, for example acetic acid, in the presence of molecular sieves and in a suitable solvent such as methanol.

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

Compounds of formula (XIII) may be prepared by reaction of a compound of formula (XIV),

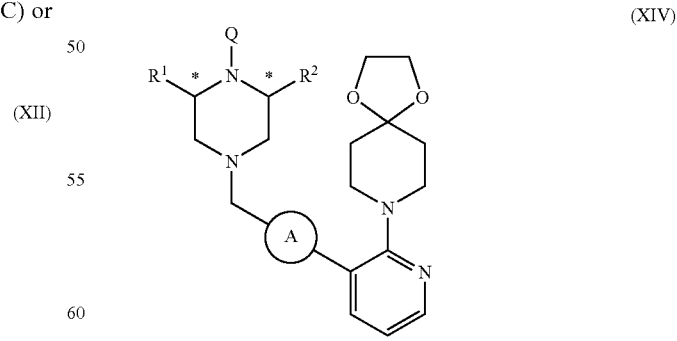

(XIV)

wherein A, R¹ and R² are as defined in relation to formula (I) and Q is hydrogen or a suitable nitrogen protecting group such as benzyloxycarbonyl (CBZ), tert-butyloxycarbonyl (BOC) or trifluoroacetyl, with a suitable acid such as hydrochloric acid, in a suitable solvent such as acetone.

Compounds of formula (XIV) may be prepared by reaction of a compound of formula (XV),

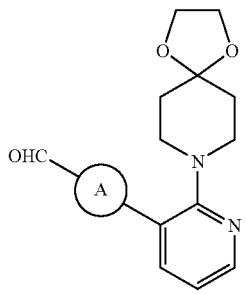

(XV)

wherein A is as defined in relation to formula (I), with an appropriately substituted piperazine (III),

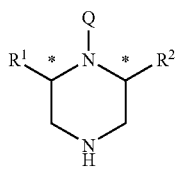

(III)

wherein $R^1$ and $R^2$ are as defined in relation to formula (I) and Q is hydrogen or a suitable nitrogen protecting group such as benzyloxycarbonyl (CBZ), tert-butyloxycarbonyl (BOC) or trifluoroacetyl, in reaction conditions suitable for a reductive alkylation, for example in the presence of a reducing agent such as sodium tri(acetoxy)borohydride in a suitable solvent such as dichloromethane or 1,2-dichloroethane.

Compounds of formula (XV) may be prepared by reaction of a compound of formula (XVI),

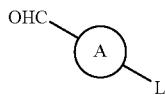

(XVI)

wherein A is as defined in relation to formula (I) and L is a suitable leaving group such as bromine or chlorine, with a compound of formula (XVII),

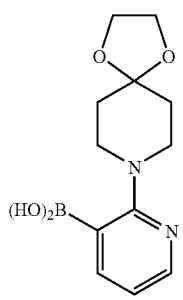

(XVII)

in the presence of a suitable base such as sodium carbonate, in the presence of suitable catalyst such as tetrakis(triphenylphosphine)palladium (0), in a suitable solvent such as a (1:1) mixture of water and 1,2 dimethoxyethane.

An alternative process for the preparation of compounds of formula (XIV) comprises reaction of a compound of formula (XI),

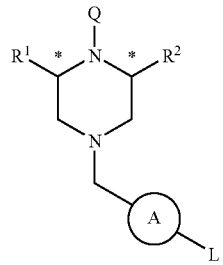

(XI)

wherein A, $R^1$ and $R^2$ are as defined in relation to formula (I), L is a leaving group such as chlorine or bromine and Q is hydrogen or a suitable nitrogen protecting group such as benzyloxycarbonyl (CBZ), tert-butyloxycarbonyl (BOC) or trifluoroacetyl, with a compound of formula (XVII),

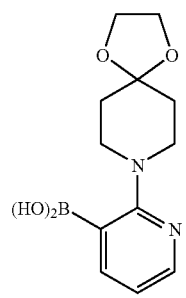

(XVII)

in the presence of a suitable base such as sodium carbonate, in the presence of suitable catalyst such as tetrakis(triphenylphosphine)palladium (0), in a suitable solvent such as a (1:1) mixture of water and 1,2 dimethoxyethane.

It will be appreciated by those skilled in the art that it may be necessary to protect certain reactive substituents during some of the above procedures. Standard protection and deprotection techniques, such as those described in Greene T. W. Protective groups in organic synthesis, New York, Wiley (1981), can be used. For example, primary amines can be protected as phthalimide, benzyl, tert-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as tert-butyloxycarbonyl may be removed using an acid such as hydrochloric or trifluoroacetic acid in a suitable solvent such as dichloromethane, diethylether, isopropanol or mixtures thereof.

Pharmaceutically acceptable salts may be prepared conventionally by reaction with the appropriate acid or acid derivative.

The present invention also provides compounds of formula (II), (XIII) and (XIV) shown above in which $R^1$, $R^2$, $R^3$, A and Y are as defined in relation to formula (I) and Q is hydrogen or a nitrogen protecting group. The invention further provides compounds of formula (IV), (VIII), (XII), (XV) and (XVII) as shown above in which $R^1$, $R^2$, $R^3$, A and Y are as defined in relation to formula (I), L is a leaving group such as bromine or chlorine and Q is hydrogen or a nitrogen protecting group. Those compounds are useful as intermediates in the preparation of compounds of the present invention.

The potencies and efficacies of the compounds of this invention for GPR38 can be determined by FLIPR assay performed on the human cloned receptor as described herein. It has been found, using the FLIPR functional assay, that compounds of formula (I) appear to be partial or full agonists of the GPR38 receptor.

The potencies and intrinsic activities of the compounds of this invention can also be determined according to the [35S] GTPγS functional assay which is described herein. It has been found, using the [35S]GTPγS functional assay, that compounds of formula (I) appear to be partial or full agonists of the GPR38 receptor.

Compounds of formula (I) and their pharmaceutically acceptable salts are therefore of use in the treatment of conditions or disorders which are mediated by compounds acting at the GPR38 receptor. In particular the compounds of formula (I) and their pharmaceutically acceptable salts are of use in the treatment of certain gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, Crohn's disease, colitis, cachexia associated with advanced diseases such as cancer and/or the treatment thereof, and other disorders such as incontinence (herein after referred to as the "Disorders of the Invention").

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions/disorders which can be mediated via the GPR38 receptor. In particular the invention provides a compound of formula (I) or a pharmaceutically acceptable salt thereof for use as a therapeutic substance in the treatment of gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, Crohn's disease, colitis, cachexia associated with advanced diseases such as cancer and/or the treatment thereof, and other disorders such as incontinence The invention further provides a method of treatment of conditions or disorders in mammals including humans which can be mediated via the GPR38 receptor, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the GPR38 receptor In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

The compounds of the present invention may be used in combination preparations. For example, the compounds of the invention may be used in combination with one or more compounds with activity in reducing gastric acid; one or more compounds with activity in reducing gastro-esophageal reflux; one or more compounds with activity in reducing esophago-gastric irritancy or inflammation, especially when used to alleviate erosive or non-erosive esophagitis; one or more compounds with analgesic activity; and/or one or more compounds with mixed activity on motility and pain.

Examples of compounds with activity in reducing gastric acid include H2 receptor antagonists, acid pump antagonists and proton pump inhibitors. Examples of compounds with activity in reducing gastro-esophageal reflux include agonists at GABA-B. Examples of compounds with analgesic activity include compounds active at Neurokinin receptors (NK1, 2, 3), TRPV1 and sodium-channels. Examples of compounds with mixed activity on motility and pain include CRF2 antagonists, 5-HT3 antagonists or octreotide or other molecules active at sst2 receptors.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Conditions, Hardware and Software for Analytical LCMS Systems

Hardware

Agilent 1100 Gradient Pump
Agilent 1100 Autosampler
Agilent 1100 DAD Dectector
Agilent 1100 Degasser
Agilent 1100 Oven
Agilent 1100 Controller
Waters ZQ Mass Spectrometer
Sedere Sedex 55, Sedere Sedex 85 or Polymer Labs PL-ELS-2100

Software

Waters MassLynx version 4.0 SP2

Column

The column used is a Waters Atlantis, the dimensions of which are 4.6 mm×50 mm. The stationary phase particle size is 3 μm.

Solvents

A: Aqueous solvent=Water+0.05% Formic Acid
B: Organic solvent=Acetonitrile+0.05% Formic Acid Method The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

Flow Rate

The above method has a flow rate of 3 ml/mins

Patent Information for Open Access Mass Directed Auto Prep System (MDAP)

Hardware

Open Access Mass Directed Prep instruments consist of the following:
1 Waters 600 Gradient pump
1 Waters 2767 inject/collector
1 Waters Reagent manager
1 MicroMass ZQ Mass Spectrometer
1 Gilson Aspec—waste collector
1 Gilson 115 post-fraction UV detector
1 Computer System.

Software

MicroMass MassLynx v4.0

Column

The column used is typically a Supelco LCABZ++ column whose dimensions are 20 mm internal diameter by 100 mm in length. The stationary phase particle size is 5 μm.

Solvents

A: Aqueous solvent=Water+0.1% Formic Acid
B: Organic solvent=MeCN:Water 95:5+0.05% Formic Acid Make up solvent=MeOH:Water 80:20+50 mMol Ammonium Acetate
Needle rinse solvent=MeOH:Water:DMSO 80:10:10
Methods One of five methods may be used depending on the analytical retention time of the compound of interest.

All have a 15-minute runtime, which comprises of a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B
Flow Rate All of the above methods have a flow rate of 20 ml/min.
Conditions used for NMR
Hardware
Bruker 400 MHz Ultrashield
Bruker B-ACS60 Autosampler
Bruker Advance 400 Console
Bruker DPX250
Bruker AVANCE 500
Bruker DRX600
Software
User interface—NMR Kiosk
Controlling software—XWin NMR version 3.0
Chromatography Unless stated otherwise, all column chromatography was carried out using silica gel columns
Abbreviations
HCl—hydrochloric acid, hydrogen chloride
$H_2SO_4$—sulfuric acid
$NaHCO_3$—sodium hydrogen carbonate
$Na_2SO_4$—sodium sulfate
1,2-DCE—1,2-dichloroethane,
NaOH—sodium hydroxide
KOH—potassium hydroxide
DCM—dichloromethane
DMF—N,N-dimethylformamide
DMSO—dimethylsulfoxide
DEAD—diethylazodicarboxylate
THF—tetrahydrofuran
MeOH—methanol,
EtOAc—ethyl acetate
$MgSO_4$—magnesium sulfate
$NH_3$—ammonia
TFA—trifluoroacetic acid
$Et_2O$—diethyl ether
$CDCl_3$—deuterochloroform
BINAP—(±)-2,2'-bis(diphenylphosphino)-1,1'-binaphthalene
dppf—1,1'-bis(diphenylphosphino)ferrocene
DIBAL-H—diisobutylaluminium hydride Description 1

1,1-Dimethylethyl 4-[(4-fluorophenyl)amino]-1-piperidinecarboxylate (D1)

A solution of 1-(tert-butoxycarbonyl)piperidin-4-one (1 g, 5 mmol), 4-fluoroaniline (0.56 g, 5 mmol) and acetic acid (0.286 ml, 5 mmol) in 1,2-dichloroethane (30 ml) was stirred at room temperature for 24 h. Sodium (triacetoxy)borohydride (1.48 g, 7 mmol) was then added and stirring continued for 24 h. The reaction mixture was washed with water, dried ($MgSO_4$) and then concentrated in vacuo to give the title compound as a solid (1.44 g). $\delta_H$ ($CDCl_3$) 1.30 (2H, m), 1.46 (9H, s), 2.02 (2H, m), 2.91 (2H, m), 3.35 (1H, m), 4.04 (2H, m), 6.54 (2H, dd), 6.88 (2H, t).

Description 2

N-(4-Fluorophenyl)-4-piperidinamine (D2)

A solution of D1 (1.44 g) in 2M HCl (5 ml) and 1,4-dioxane (20 ml) was heated at 60° C. for 24 h. On cooling, the solution was diluted with water, basified with 2M NaOH solution and extracted with EtOAc (×3). The combined organics were dried ($MgSO_4$) and concentrated in vacuo to give the title compound as a yellow oil (0.71 g). $\delta_H$ ($CDCl_3$) 1.29 (2H, m), 2.05 (2H, m), 2.70 (2H, m), 3.20 (1H, m), 3.30 (2H, m), 6.54 (2H, dd), 6.88 (2H, t).

The following intermediates D3-D4 were prepared from the appropriate aniline using the methods outlined in Descriptions 1 and 2.

N-(3-Fluorophenyl)-4-piperidinamine (D3)

N-(2-Fluorophenyl)-4-piperidinamine (D4)

Description 5

1,1-Dimethylethyl 3-methyl-1H-pyrazole-1-carboxylate (D5)

3-Methylpyrazole (4.04 g, 49.8 mmol) in acetonitrile (50 ml) was cooled to 0° C. and di-tert-butyl dicarbonate (13.00 g, 59.6 mmol) was added followed by 4-dimethyl-aminopyridine (0.61 g, 4.98 mmol). After 2 h, the solution was diluted with EtOAc (50 ml) and washed with 1M HCl, saturated $NaHCO_3$ solution and brine (100 ml each), dried ($Na_2SO_4$) and concentrated. Purification by column chromatography on silica (0-50% diethyl ether\40-60 pet. ether gradient) gave the title compound as an oil (6.35 g). $\delta_H$ ($CDCl_3$) 1.64 (9H, s), 2.33 (3H, s), 6.22 (1H, d), 8.13 (1H, d).

Description 6

1,1-Dimethylethyl 3-(bromomethyl)-1H-pyrazole-1-carboxylate (D6)

D5 (2 g, 10.97 mmol), N-bromosuccinimide (2.94 g, 16.46 mmol) and benzoyl peroxide (0.57 g, 1.65 mmol) were dissolved in carbon tetrachloride (40 ml) and heated to 80° C. for 3 h. The mixture was diluted with EtOAc (60 ml) and washed with saturated $NaHCO_3$ solution and brine (100 ml each), dried ($Na_2SO_4$) and concentrated. Purification by column chromatography on silica (0-50% diethyl ether\40-60 pet. ether gradient) gave the title compound as a yellow oil (1.58 g). $\delta_H$ ($CDCl_3$) 1.65 (9H, s), 4.49 (2H, s), 6.47 (1H, d), 8.03 (1H, d).

Description 7

1,1-Dimethylethyl 3-{[(3R,5S)-3,5-dimethyl-1-piperazinyl]methyl}-1H-pyrazole-1-carboxylate (D7)

D6 (1.67 g, 6.41 mmol), (2R,6S)-2,6-dimethylpiperazine (0.73 g, 6.41 mmol) and potassium carbonate (1.95 g, 14.1 mmol) in DMF (20 ml) were heated at 50° C. for 2 h. The mixture was concentrated and the residue partitioned between DCM and water (50 ml each). The aqueous layer was re-extracted with DCM (50 ml) and the combined organics washed with brine (100 ml), dried (Na$_2$SO$_4$) and concentrated to yield the title compound as an orange oil (1.88 g). $\delta_H$ (CDCl$_3$) 1.25 (6H, d), 1.15 (1H, br s), 1.64-1.71 (11H, m), 2.77 (2H, m), 2.93 (2H, m), 3.59 (2H, s), 6.40 (1H, d), 8.00 (1H, d). MS (ES): MH$^+$ 295

Description 8

1,1-Dimethylethyl 3-{[(3R,5S)-3,5-dimethyl-4-(trifluoroacetyl)-1-piperazinyl]methyl}-1H-pyrazole-1-carboxylate (D8)

D7 (1.88 g, 6.39 mmol) and 2,6-lutidine (1.49 ml, 12.78 mmol) in DCM (30 ml) at 0° C. were treated with trifluoroacetic anhydride (0.89 ml in 7.5 ml DCM, 6.39 mmol), added dropwise over 5 min. The solution was allowed to warm to 25° C. and stirred for 16 h. The mixture was washed with 10% citric acid and brine (40 ml each), dried (Na$_2$SO$_4$) and concentrated to yield the title compound as an orange oil (2.36 g). $\delta_H$(CDCl$_3$) 1.43 (6H, s), 1.65 (9H, s), 2.31 (2H, dd), 2.75 (2H, d), 3.65 (2H, s), 4.12 (1H, s), 4.53 (1H, s), 6.46 (1H, d), 8.15 (1H, d).

Description 9

(2R,6S)-2,6-Dimethyl-4-(1H-pyrazol-3-ylmethyl)-1-(trifluoroacetyl)piperazine (D9)

D8 (2.20 g, 5.63 mmol) was taken up in 25% TFA in DCM (50 ml) and stirred for 4 h at 25° C. The solvent was removed in vacuo and the residue dissolved in DCM (50 ml), washed with saturated NaHCO$_3$, dried (Na$_2$SO$_4$) and concentrated to yield the title compound as an orange foam (1.64 g). $\delta_H$ (CDCl$_3$) 1.43 (6H, d), 2.48 (2H, dd), 2.97 (2H, d), 3.88 (2H, s), 4.15-4.75 (2H, br d), 6.40 (1H, d), 7.64 (1H, d), 8.93 (1H, br s). MS (ES): MH$^+$ 291.

Description 10

1-(3-Bromo-2-pyridinyl)-N-(4-fluorophenyl)-4-piperidinamine (D10)

2-Chloro-3-bromopyridine (0.25 g, 1.3 mmol), D2 (0.25 g, 1.3 mmol) and potassium carbonate (0.23 g, 2.9 mmol) in DMF (5 ml) were heated at 120° C. for 16 h. The mixture was concentrated and the residue partitioned between EtOAc and water (50 ml each). The aqueous was re-extracted with EtOAc (50 ml) and the combined organics washed with water, dried (Na$_2$SO$_4$) and concentrated. Purification by column chromatography on silica (0-50% diethyl ether\40-60 pet. ether gradient) gave the title compound as a yellow solid (0.26 g). $\delta_H$ (CDCl$_3$) 1.64 (2H, m), 2.17 (2H, d), 2.98 (2H, m), 3.43 (2H, m), 3.74 (2H, m), 6.58 (2H, m), 6.77 (1H, m), 6.89 (2H, m), 7.78 (1H, d), 8.22 (1H, dd). MS (ES): MH$^+$ 351.

The following intermediates D11-D12 were prepared in a manner similar to that described for Description 10

1-(3-Bromo-2-pyridinyl)-N-(3-fluorophenyl)-4-piperidinamine (D11)

1-(3-Bromo-2-pyridinyl)-N-(2-fluorophenyl)-4-piperidinamine (D12)

Description 13

1-[3-(3-{[(3R,5S)-3,5-Dimethyl-4-(trifluoroacetyl)-1-piperazinyl]methyl}-1H-pyrazol-1-yl)-2-pyridinyl]-N-(4-fluorophenyl)-4-piperidinamine (D13)

D9 (0.96 g, 3.30 mmol), D10 (1 g, 2.86 mmol), copper (I) iodide (0.02 g, 0.11 mmol), potassium carbonate (0.48 g, 3.47 mmol), and L-proline (0.04 g, 0.35 mmol) in DMSO (6 ml) were heated to 170° C. in a microwave reactor for 6 h. The mixture was partitioned between DCM and water (25 ml each) and the aqueous layer re-extracted with 10% MeOH in DCM (25 ml). The combined organic layers were washed with water (50 ml), dried (Na$_2$SO$_4$) and concentrated. Purification by column chromatography on silica (0-25% EtOAc\40-60 pet. ether gradient) gave the title compound as an orange foam (0.56 g). $\delta_H$ (CDCl$_3$) 1.21-1.28 (8H, br t), 2.03 (2H, d), 2.30 (2H, dd), 2.81 (4H, m), 3.30 (4H, m), 3.67 (2H, s), 4.13 (1H, br s), 4.53 (1H, br s), 6.45 (1H, d), 6.53 (2H, m), 6.87 (2H, m), 6.98 (1H, m), 7.71 (1H, m), 7.99 (1H, d), 8.26 (1H, m). MS (ES): MH$^+$ 560.

Description 14

8-(3-Bromo-2-pyridinyl)-1,4-dioxa-8-azaspiro[4.5]decane (D14)

The title compound was prepared from 2-chloro-3-bromopyridine and 1,4-dioxa-8-azaspiro[4,5]decane in a manner similar to that of Description 10.

Description 15

[2-(1,4-Dioxa-8-azaspiro[4.5]dec-8-yl)-3-pyridinyl]boronic acid (D15)

D14 (1.0 g, 3.3 mmol) in dry diethyl ether (10 ml) was added dropwise to a solution of n-butyllithium (1.6 ml, 4.0 mmol, 2.5M in hexanes) in dry diethyl ether (40 ml) at −78° C. The mixture was stirred for 2 h, then tri-isopropyl borate (0.75 g, 4.0 mmol) in diethyl ether (10 ml) was added dropwise over 10 min and the mixture allowed to warm to 25° C. The mixture was stirred for 16 h, slowly quenched with 5% NaOH (20 ml) and stirred for 30 min. The aqueous layer was cooled to <5° C., adjusted to pH6 with 2M HCl and the product extracted into EtOAc (×2). The combined organic layers were dried and concentrated to give the title compound as a yellow oil (0.53 g). $\delta_H$ (CDCl$_3$) 1.94 (4H, m), 3.47 (4H, m), 4.01 (4H, s), 7.08 (1H, m), 7.67 (1H, dd), 7.84 (1H, dd). MS (ES): MH$^+$ 265

Description 16

8-[3-(5-Formyl-1,3-thiazol-2-yl)-2-pyridinyl]-1,4-dioxa-8-azaspiro[4.5]decane (D16)

D15 (250 mg, 0.95 mmol), sodium carbonate (401 mg, 3.79 mmol), 2-bromo-1,3-thiazole-5-carboxaldehyde (182 mg, 0.95 mmol) and tetrakistriphenylphosphine Pd(0) (55 mg, 0.047 mmol) in 1:1 aqueous 1,2-dimethoxyethane (4 ml) was heated in a microwave reactor at 150° C. for 5 min and the solvent was then removed in vacuo. The residue was partitioned between water and DCM and the organic phase was dried and concentrated to give the crude product as an oil which was purified on silica (0-100% diethyl ether/pet. ether gradient) to give the title compound as a yellow solid (85 mg). $\delta_H$ (CDCl$_3$) 1.96 (4H, m), 3.28 (4H, m), 4.00 (4H, s), 7.13 (1H, m), 8.42 (1H, dd), 8.44 (1H, s), 8.48 (1H, dd), 10.10 (1H, s). MS (ES): MH$^+$ 332.

Description 17

8-[3-(5-{[(3R,5S)-3,5-Dimethyl-1-piperazinyl]methyl}-1,3-thiazol-2-yl)-2-pyridinyl]-1,4-dioxa-8-azaspiro[4.5]decane (D17)

D16 (85 mg, 0.26 mmol) and (2R,6S)-2,6-dimethylpiperazine (29 mg, 0.26 mmol) in 1,2-dichloroethane (2 ml) were stirred at 50° C. for 3 h. The mixture was cooled in an ice bath and sodium (triacetoxy)borohydride (82 mg, 0.39 mmol) was added. The resulting mixture was stirred at room temp. overnight then diluted with DCM. The organic phase was separated and washed with saturated NaHCO$_3$ solution, then dried and concentrated to give the title compound as a yellow oil (118 mg). δ$_H$ (CDCl$_3$) 1.08 (6H, d), 1.78 (2H, br t), 1.91 (4H, m), 2.83 (2H, m), 3.00 (2H, m), 3.25 (4H, m), 3.73 (4H, s), 3.98 (2H, s), 7.04 (1H, dd), 7.63 (1H, s), 8.25 (1H, dd), 8.32 (1H, dd). MS (ES): MH$^+$ 430.

Description 18

1-[3-(5-{[(3R,5S)-3,5-Dimethyl-1-piperazinyl]methyl}-1,3-thiazol-2-yl)-2-pyridinyl]-4-piperidinone (D18)

D17 (118 mg, 0.26 mmol) in water (3.5 ml) containing c.H$_2$SO$_4$ (40 mg) was heated at 100° C. for 1 h; the mixture was basified to pH 11 with sodium carbonate and the product extracted into EtOAc (×3). Purification by column chromatography on silica eluting with a 0-10% [MeOH/NH$_3$ (9:1)]/DCM gradient gave the title compound (38 mg). MS (ES): MH$^+$ 386.

Description 19

5-(2-{4-[(4-Fluorophenyl)amino]-1-piperidinyl}-3-pyridinyl)-2-furancarbaldehyde (D19)

D10 (250 mg, 0.72 mmol), 5-formylfuran-2-ylboronic acid (100 mg, 0.72 mmol), sodium carbonate (227 mg, 2.15 mmol) and PdCl$_2$-[dppf] (29 mg, 0.04 mmol) in DMF (5 ml) were heated at 80° C. for 20 h. A further portion of 5-formylfuran-2-ylboronic acid (100 mg, 0.72 mmol) was added and heating continued for 1 day, then the mixture was concentrated in vacuo. The residue was dissolved in EtOAc, washed with saturated NaHCO$_3$ and brine, then dried (Na$_2$SO$_4$) and concentrated in vacuo. The crude product was purified by column chromatography on silica (0-100% diethyl ether/pet. ether gradient] to give the title compound as an oily solid (85 mg). δ$_H$ (CDCl$_3$) 1.59 (2H, m), 2.14 (2H, m), 2.98 (2H, m), 3.40 (1H, m), 3.53 (2H, br d), 6.57 (2H, dd), 6.89 (2H, t), 7.00 (1H, dd), 7.17 (1H, d), 7.34 (1H, d), 8.10 (1H, dd), 8.30 (1H, m), 9.65 (1H, s). MS (ES): MH$^+$ 366.

Description 20

4-(2-{4-[(4-Fluorophenyl)amino]-1-piperidinyl}-3-pyridinyl)-2-thiophene carbaldehyde (D20)

D10 (100 mg, 0.29 mmol), (5-formyl-2-thienyl) boronic acid (334 mg, 2.1 mmol), tetrakis(triphenylphosphine)palladium(0) (16 mg, 0.014 mmol) and sodium carbonate (121 mg, 1.1 mmol) were suspended in a mixture of 1,2-dimethoxyethane (2 ml) and water (2 ml). The reaction mixture was heated in a Biotage Initiator Sixty Microwave at 110° C. for 20 minutes. The reaction mixture was concentrated and the residue partitioned between DCM and water (5 ml each). The aqueous was re-extracted with DCM (5 ml) and the combined organics washed with water, dried (Na$_2$SO$_4$) and concentrated. Purification by column chromatography on silica (0-100% EtOAc/40-60 petrol ether gradient) gave the title compound as a yellow oil (0.078 g). δ$_H$ (CDCl$_3$) 1.57 (3H, m), 2.09 (1H, m), 2.93 (2H, m), 3.32-3.50 (4H, m), 6.55 (2H, dd), 6.87 (2H, t), 6.99 (1H, dd), 7.49 (1H, d), 7.72 (2H, m), 8.3 (1H, dd), 9.93 (1H, s). MS (ES): MH$^+$ 382.

Description 21

2-Bromo-1,3-thiazole-4-carbaldehyde (D21)

Ethyl 2-bromothiazole-4-carboxylate (3 g, 12.7 mmol) was taken up in THF and dichloromethane (100 ml each) and cooled to −78° C. 1M DIBAL-H in hexanes (25.4 ml, 25.4 mmol) was added dropwise maintaining the temperature at <−70° C. The solution was stirred for 5 h and quenched with MeOH (20 ml). The solution was allowed to warm to room temperature, poured into 1M HCl (200 ml) and extracted with EtOAc (3×100 ml). The combined organics were washed with brine (300 ml), dried (Na$_2$SO$_4$) and concentrated. Purification by column chromatography on silica (0-50% EtOAc\40-60 pet. ether gradient) yielded the product as a white solid (0.862 g). δ$_H$ (CDCl$_3$) 8.10 (1H, s), 9.95 (1H, s).

Description 22

2-[2-(1,4-Dioxa-8-azaspiro[4.5]dec-8-yl)-3-pyridinyl]-1,3-thiazole-4-carbaldehyde (D22)

D21 (250 mg, 1.30 mmol), D15 (343 mg, 1.30 mmol), tetrakis(triphenylphosphine)palladium (0) (75 mg, 0.06 mmol), and sodium carbonate (552 mg, 5.2 mmol) were combined in 1,2-dimethoxyethane and water (2.5 ml each), then heated to 175° C. in a microwave reactor for 12 mins. The mixture was partitioned between DCM and water (10 ml each) and the organic layer re-extracted with DCM (10 ml). The combined organics were dried (Na$_2$SO$_4$) and concentrated. Purification by column chromatography on silica (0-100% diethyl ether\40-60 pet. ether gradient) gave the product as an orange solid (694 mg). δ$_H$ (CDCl$_3$) 1.91 (4H, m), 3.27 (4H, m), 4.00 (4H, s), 7.09 (1H, m), 8.22 (1H, s), 8.4 (1H, m), 8.45 (1H, m), 10.10 (1H, s). MS (ES): MH$^+$ 332.

Description 23

8-[3-(4-{[(3R,5S)-3,5-Dimethyl-1-piperazinyl]methyl}-1,3-thiazol-2-yl)-2-pyridinyl]-1,4-dioxa-8-azaspiro[4.5]decane (D23)

D22 (694 mg, 2.09 mmol) and ((2R,6S)-2,6-dimethylpiperazine (240 mg, 2.09 mmol) were combined in 1,2-dichloroethane (30 ml) and heated to 50° C. for 3 h. The solution was cooled to 0° C. and sodium tri(acetoxy)borohydride (888 mg, 4.18 mmol) was added. The mixture was stirred for 16 h then diluted with DCM (50 ml) and washed with water and brine (100 ml each). The organics were dried and concentrated. Purification by column chromatography on silica [0-10% (2M NH$_3$ in MeOH)\DCM gradient] yielded the product as an orange oil (747 mg). δ$_H$ (CDCl$_3$) 1.06 (6H, d), 1.6 (1H, br s), 1.81 (2H, t), 1.91 (2H, t), 2.94 (2H, m), 3.02 (2H, m), 3.25 (4H, t), 3.73 (2H, s), 3.90 (4H, s), 7.04 (1H, m), 7.18 (1H, s), 8.28 (1H, m), 8.32 (1H, s). MS (ES): MH$^+$ 430.

Description 24

1-[3-(4-{[(3R,5S)-3,5-Dimethyl-1-piperazinyl]methyl}-1,3-thiazol-2-yl)-2-pyridinyl]-4-piperidinone (D24)

D23 (747 mg, 1.74 mmol) and 98% H$_2$SO$_4$ (261 mg, 2.61 mmol) were combined in water and heated to 100° C. for 2 hrs. The solution was cooled and basified with sodium carbonate. The mixture was extracted with DCM (3×20 ml) and the combined organics dried and concentrated in vacuo. Purification by column chromatography on silica [0-10% (2M NH$_3$ in MeOH)\DCM gradient] yielded the product as an orange oil (124 mg). δ$_H$ (CDCl$_3$) 1.05 (6H, d), 1.78 (2H, t), 2.00 (1H, br s), 2.66 (4H, t), 2.92 (2H, m), 3.00 (2H, m), 3.49 (4H, t), 3.70 (2H, s), 7.17 (2H, m), 8.32 (1H, s), 8.37 (1H, d). MS (ES): MH$^+$ 386.

Description 25

6-Chloro-3-pyridinecarbaldehyde (D25)

2-Chloro-5-cyanopyridine (5 g, 36 mmol) was dissolved in anhydrous toluene (100 ml) and cooled to 5° C. 1.5M DIBAL-H in toluene (25.2 ml, 38 mmol) was added dropwise over 20 min. The resulting solution was treated with MeOH (10 ml) and then 2M H$_2$SO$_4$ (30 ml) and stirred at room temp. for 48 h. The mixture was concentrated and the residue partitioned between EtOAc and water. The organic layer was separated, washed with brine and saturated NaHCO$_3$ solution, then dried (Na$_2$SO$_4$) and concentrated to give the title compound as a pale yellow solid (5.419). δ$_H$ (CDCl$_3$) 7.51 (1H, d), 8.14 (1H, m), 8.87 (1H, d), 10.10 (1H, s).

Description 26

(3R,5S)-1-[(6-Chloro-3-pyridinyl)methyl]-3,5-dimethylpiperazine (D26)

D25 (0.5 g, 3.5 mmol) and (2R,6S)-dimethylpiperazine (0.40 g, 3.5 mmol) were dissolved in 1,2-dichloroethane and stirred at room temp. for 24 h. Sodium tri(acetoxy)borohydride was added and the mixture was stirred at room temp. for a further 4 h. The reaction mixture was washed with saturated NaHCO$_3$ solution, and then water. The organic layer was separated, dried (NaSO$_4$) and concentrated. Purification by column chromatography on silica [0-10% (2M NH$_3$ in MeOH)/DCM gradient] gave the title compound as a pale yellow solid (0.45 g). δ$_H$ (CDCl$_3$) 1.02 (6H, d), 1.64 (2H, t), 2.70 (2H, m), 2.91 (2H, m), 3.46 (2H, s), 7.29 (1H, d), 7.66 (1H, d), 8.30 (1H, s). MS (ES): MH$^+$ 240.

Description 27

5-{[(3R,5S)-3,5-Dimethyl-1-piperazinyl]methyl}-2'-(1,4-dioxa-8-azaspiro[4.5]dec-8-yl)-2,3'-bipyridine (D27)

D15 (0.5 g, 1.90 mmol), D26 (0.45 g, 1.90 mmol), sodium carbonate (0.8 g, 7.58 mmol) and tetrakis(triphenylphosphine)palladium (0) (0.11 g, 0.1 mmol) were dissolved in 1:1 aqueous 1,2-dimethoxyethane (12 ml) and heated at 150° C. for 5 min in a microwave reactor. The mixture was concentrated and the residue partitioned between DCM and water. The aqueous layer was re-extracted with DCM. The combined organics were dried (NaSO$_4$) and concentrated. Purification by column chromatography on silica [0-10% (2M NH$_3$ in MeOH)/DCM gradient] gave the title compound as an orange oil (0.62 g). δ$_H$ (CDCl$_3$) 1.05 (6H, m), 1.67 (4H, m), 2.73 (3H, m), 2.94 (3H, m), 3.22 (4H, t), 3.53 (2H, s), 3.93 (4H, s), 6.94 (1H, m), 7.70 (1H, m), 7.84 (2H, m), 8.24 (1H, m), 8.60 (1H, d). MS (ES): MH$^+$ 424.

Description 28

1-(5-{[(3R,5S)-3,5-Dimethyl-1-piperazinyl]methyl}-2,3'-bipyridin-2'-yl)-4-piperidinone (D28)

D27 (0.62 g, 1.47 mmol) and concentrated sulfuric acid (0.22 g, 2.21 mmol) were combined in water (16 ml) and heated to 80° C. for 3 h. Another portion of sulfuric acid was added (0.22 g, 2.21 mmol) and the mixture was heated at 80° C. for a further 2 h. The reaction mixture was allowed to cool to room temp. and solid Na$_2$CO$_3$ was added until the mixture reached pH 10. The aqueous mixture was extracted with EtOAc (×3). The combined organics were dried (NaSO$_4$) and concentrated to produce the title compound as a brown oil (0.57 g). δ$_H$ (CDCl$_3$) 1.03 (6H, m), 1.66 (4H, m), 2.43 (4H, t), 2.70 (1H, m), 2.76 (2H, m), 2.94 (3H, m), 3.55 (2H, s), 7.01 (1H, m), 7.73 (1H, m), 7.84 (2H, m), 8.29 (1H, m), 8.64 (1H, s). MS (ES): MH$^+$ 380.

Description 29

1,1-Dimethylethyl 4-[(3-fluorophenyl)oxy]-1-piperidinecarboxylate (D29)

To a solution of 1,1-dimethylethyl 4-hydroxy-1-piperidinecarboxylate (24 g, 112 mmol), 3-fluorophenol (5.6 g, 59 mmol) and triphenylphosphine (31.4 g, 118 mmol) in THF (100 ml) was added di-isopropylazodicarboxylate (23.3 ml, 118 mmol). The reaction was stirred at room temperature for 3 days and then the solvent removed in vacuo. The residue was diluted with DCM, hexane was added and the resultant white precipitate filtered off. The filtrate was concentrated in vacuo and purified by chromatography. Elution with DCM gave the title compound (16.4 g, 87% pure). δ$_H$ (CDCl$_3$, 250 MHz) 1.47 (9H, s), 1.76 (2H, m), 1.92 (2H, m), 3.35 (2H, ddd), 3.69 (2H, ddd), 4.44 (1H, m), 6.65 (3H, m), 7.20 (1H, m).

Description 30

4-[(3-Fluorophenyl)oxy]piperidine (D30)

A solution of D29 (16.4 g, 55 mmol) in DCM (200 ml) at 0° C. was treated drop-wise with TFA (17 ml). The reaction was warmed to room temperature for 2.5 hrs and left overnight. The solvent was then removed in vacuo and the residue partitioned between DCM and 2M NaOH solution. The aqueous was further extracted with DCM (×2) and the combined organics concentrated in vacuo. The residue was redissolved in DCM and extracted with 2M HCl (×2) which was then basified and re-extracted with DCM. The combined organics were concentrated in vacuo to give the title compound (12 g). δ$_H$ (CDCl$_3$, 250 MHz) 1.66 (2H, m), 2.01 (2H, m), 2.73 (2H, m), 3.14 (2H, m), 4.34 (1H, m), 6.68 (3H, m), 7.19 (1H, m), MS (ES): MH$^+$ 196. This whole was diluted with MeOH and treated with 1M HCl in Et$_2$O to give the hydrochloride salt of the title compound (8.0 g).

Description 31

4-[(4-Fluorophenyl)oxy]piperidine (D31)

The title compound may be prepared using a method similar to that described in L. C Blumberg, M. F. Brown, M. M. Hayward and C. S. Poss, PCT Int. Appl., WO 2004009550.

Description 32

Phenylmethyl (2S)-4-[(1-{[(1,1-dimethylethyl)oxy]carbonyl}-1H-pyrazol-3-yl)methyl]-2-methyl-1-piperazinecarboxylate (D32)

D6 (1.368 g, 5.24 mmol), piperazine (1.228 g, 5.24 mmol) and potassium carbonate (1.593 g, 11.53 mmol) were combined in DMF (20 ml) and heated to 50° C. for 2 h. The mixture was concentrated and the residues partitioned between DCM and water. The aqueous layer was re-extracted with DCM and the combined organics were washed with brine, dried with sodium sulfate and concentrated to yield the product as an orange oil (2.2 g). $^1$H NMR (CDCl$_3$): δ 1.26-1.27 (3H, d), 1.64 (9H, s), 2.09-2.16 (2H, m), 2.21-2.24 (2H, m), 2.59-2.62 (2H, d), 2.77-2.80 (2H, d), 3.15-3.22 (2H, m), 3.52-3.63 (2H, q), 3.89-3.93 (1H, d), 4.29 (1H, bs), 5.09-5.16 (2H, m), 6.40-6.41 (1H, d), 7.29-7.38 (5H, m), 8.00-8.01 (1H, d), MS (ES): MH$^+$ 415.3

Description 33

Phenylmethyl (2S)-2-methyl-4-(1H-pyrazol-3-ylmethyl)-1-piperazinecarboxylate (D33)

D32 (2.20 g, 5.24 mmol) was taken up in 20% TFA in DCM (35 ml) and stirred for 2 h. An additional portion of TFA (2 ml) was added and stirring continued for 2 h. The solvent was stripped off and the residues partitioned between DCM and sat. sodium bicarbonate. The organic layer was isolated and washed with sat. sodium bicarbonate, dried with sodium sulfate and concentrated to yield the product as a yellow oil (1.394 g). $^1$H NMR (CDCl$_3$): δ 1.26-1.28 (3H, d), 2.04-2.11 (1H, m), 2.17-2.24 (1H, m), 2.61-2.63 (1H, m), 2.78-2.81 (2H, dd), 3.15-3.23 (1H, m), 3.51-3.63 (2H, q), 3.90-3.94 (1H, d), 4.30 (1H, bs), 5.10-5.17 (2H, m), 6.21-6.22 (1H, d), 7.29-7.38 (5H, m), 7.52-7.53 (1H, d), 10.28 (1H, bs), MS (ES): MH$^+$ 315.3

Description 34

1-(3-bromo-2-pyridinyl)-4-piperidinol (D34)

3-Bromo-2-chloropyridine (5.95 g, 30.92 mmol), 4-hydroxypiperidine (5 g, 49.43 mmol) and potassium carbonate (15.03 g, 108.75 mmol) were combined in DMF (200 ml) and heated to 120° C. overnight. The solvent was removed and the residues partitioned between EtOAc and water. The aqueous layer was re-extracted with EtOAc and the combined organics washed with water, dried and concentrated. The crude product was purified by column chromatography. Elution with 20-75% EtOAc/pet. ether yielded the product as a yellow oil (5.1 g). δ$_H$ (CDCl$_3$, 400 MHz): 1.60-1.61 (1H, m), 1.68-1.79 (2H, m), 2.01-2.07 (2H, m), 2.98-3.04 (2H, m), 3.64-3.69 (2H, m), 3.86-3.91 (1H, m), 6.74-6.77 (1H, m), 7.77-7.79 (1H, dd), 8.21-8.22 (1H, m).

Description 35

3-Bromo-2-{4-[(4-fluorophenyl)oxy]-1-piperidinyl}pyridine (D35)

D34 (500 mg, 1.94 mmol), triphenylphosphine (2.14 mmol) and 4-fluorophenol (2.14 mmol) were combined in THF (12.5 ml) under Ar and cooled to 0° C. DEAD (0.34 ml, 2.14 mmol) was added portion wise over 5 min. The ice-bath was removed and stirred overnight. The solvent was removed. The crude product was purified by column chromatography. Elution with 0-25% Et$_2$O/pet. ether yielded the product as a white solid (470 mg), δ$_H$ (CDCl$_3$, 400 MHz): 1.91-2.00 (2H, m), 2.08-2.15 (2H, m), 3.15-3.21 (2H, m), 3.59-3.64 (2H, m), 4.38-4.44 (1H, m), 6.76 (1H, m), 6.88-6.92 (2H, m), 6.95-7.00 (2H, m), 7.77-7.80 (1H, dd), 8.22-8.24 (1H, m).

Description 36

3-Bromo-2-{4-[(3-fluorophenyl)oxy]-1-piperidinyl}pyridine (D36)

The title compound was prepared using a method similar to that described for D35 using 3-fluorophenol, MS (ES): MH$^+$ 352.2/353.2

Description 37

Preparation of 3-bromo-2-{4-[(2-fluorophenyl)oxy]-1-piperidinyl}pyridine (D37)

The title compound was prepared using a method similar to that described for D35 using 2-fluorophenol, MS (ES): MH$^+$ 352.2/353.2

Description 38

(2R,6S)-4-{[1-(2-{4-[(4-Fluorophenyl)oxy]-1-piperidinyl}-3-pyridinyl)-1H-pyrazol-3-yl]methyl}-2,6-dimethyl-1-(trifluoroacetyl)piperazine (D38)

D9 (116 mg, 0.40 mmol), D35 (116 mg, 0.33 mol), CuI (3 mg, 0.017 mmol), potassium carbonate (256 mgs, 1.85 mmol) and l-proline (5 mg, 0.04 mmol) were combined in DMSO (0.6 ml) and heated to 175° C. in the microwave for 12 h. The solution was partitioned between DCM and water. The aqueous was re-extracted with DCM. The combined organics were washed with water, dried and concentrated. The crude product was purified by column chromatography. Elution with 0-45% EtOAc/pet ether then 10% MeOH/DCM yielded the crude product. Elution with 50% EtOAc/pet. ether through an Isolute Flash SI column yielded the product as a brown oil (24.8 mgs). δ$_H$ (CDCl$_3$, 400 MHz): 1.35-1.50 (6H, bd), 1.70-1.79 (2H, m), 1.94-1.98 (2H, m), 2.23-2.34 (2H, m), 2.77 (2H, bs), 2.83-2.90 (2H, m), 3.23-3.27 (2H, m), 3.68 (2H, s), 4.13 (1H, bs), 4.27-4.32 (1H, m), 4.54 (1H, bs), 6.47 (1H, d), 6.81-6.86 (2H, m), 6.93-7.00 (3H, m), 7.69-7.72 (1H, dd), 8.00-8.01 (1H, d), 8.25-8.26 (1H, m), MS (ES): MH$^+$ 561.3

Description 39

(2R,6S)-4-{[1-(2-{4-[(2-Fluorophenyl)oxy]-1-piperidinyl}-3-pyridinyl)-1H-pyrazol-3-yl]methyl}-2,6-dimethyl-1-(trifluoroacetyl)piperazine (D39)

The title compound was prepared using a method similar to that described for D38 using D37, MS (ES): MH$^+$ 561.3

Description 40

(2R,6S)-4-{[1-(2-{3-[(3-Fluorophenyl)oxy]-1-piperidinyl}-3-pyridinyl)-1H-pyrazol-3-yl]methyl}-2,6-dimethyl-1-(trifluoroacetyl)piperazine (D40)

The title compound was prepared using a method similar to that described for D38 using D36, MS (ES): MH$^+$ 561.3

Description 41

Phenylmethyl (2S)-4-{[1-(2-{4-[(3-fluorophenyl)oxy]-1-piperidinyl}-3-pyridinyl)-1H-pyrazol-3-yl]methyl}-2-methyl-1-piperazinecarboxylate (D41)

The title compound was prepared in a similar manner to that described for D38 using D33 and D36, MS (ES): MH+ 585.3

Description 42

Phenylmethyl (2S)-4-{[1-(2-{4-[(4-fluorophenyl)oxy]-1-piperidinyl}-3-pyridinyl)-1H-pyrazol-3-yl]methyl}-2-methyl-1-piperazinecarboxylate (D42)

The title compound was prepared in a similar manner to that described for D38 using D33 and D35, MS (ES): MH+ 585

Description 43

2'-(1,4-Dioxa-8-azaspiro[4.5]dec-8-yl)-2,3'-bipyridine-5-carbaldehyde (D43)

D25 (0.31 g, 2.2 mmol), D15 (0.58 g, 2.2 mmol), sodium carbonate (0.93 g, 8.8 mmol) and tetrakis triphenylphosphine Pd(0) catalyst (0.13 g, 0.11 mmol) were combined in DME (7 ml) and water (7 ml) and heated using a microwave at 150° C. for 5 min. The solvent was removed under vacuum and the residue was partitioned between DCM and water. The aqueous layer was extracted (×3) with DCM. The DCM layers were combined, dried and concentrated to produce crude product as a brown oil. Product purified by column chromatography, eluting 0-50% ethyl acetate/petrol to produce title compound as a yellow solid (0.32 g), $^1$H NMR (CDCl$_3$) δ: 1.69 (4H, t), 3.27 (4H, t), 3.94 (4H, s), 6.98 (1H, m), 7.95 (1H, m), 8.13 (1H, d), 8.18 (1H, m), 8.30 (1H, dd), 9.14 (1H, s), 10.13 (1H, s), MS (ES): MH+ 326.

Description 44

Phenylmethyl (2S)-4-{[2'-(1,4-dioxa-8-azaspiro[4.5]dec-8-yl)-2,3'-bipyridin-5-yl]methyl}-2-methyl-1-piperazinecarboxylate (D44)

D43 (0.32 g, 0.98 mmol) and phenylmethyl (2S)-2-methyl-1-piperazinecarboxylate (0.23 g, 0.98 mmol) were dissolved in DCE and stirred for 5 min at 50° C. After this time, sodium triacetoxyborohydride (0.31 g, 1.47 mmol) was added and the mixture was allowed to stir overnight at 50° C. The reaction mixture was washed with sodium bicarbonate solution, then water. The organic layer was dried and concentrated to produce crude product as yellow oil. Product purified by column chromatography, eluting 0-100% ethyl acetate/petrol to produce title compound as a colourless oil (0.14 g), $^1$H NMR (CDCl$_3$) δ: 1.28 (3H, d), 1.67 (4H, t), 2.10 (1H, m), 2.22 (1H, dd), 2.61 (1H, d), 2.79 (1H, d), 3.18 (1H, m), 3.22 (4H, t), 3.44 (1H, d), 3.57 (1H, d), 3.93 (5H, m), 4.32 (1H, br), 5.14 (2H, s), 6.94 (1H, dd), 7.34 (5H, m), 7.70 (1H, dd), 7.85 (2H, m), 8.25 (1H, dd), 8.62 (1H, s), MS (ES): MH+ 544.

Description 45

Phenylmethyl (2S)-2-methyl-4-{[2'-(4-oxo-1-piperidinyl)-2,3'-bipyridin-5-yl]methyl}-1-piperazinecarboxylate (D45)

D44 (0.14 g, 0.26 mmol) was combined with concentrated sulfuric acid (0.038 g, 0.38 mmol) in water (3 ml) and heated at 80° C. for 2.5 h. The reaction mixture was cooled to rt and sodium carbonate was added until the mixture reached pH10. The mixture was extracted with ethyl acetate(×3). The organic layers were combined, dried and concentrated to produce the title compound as a pale yellow oil (0.12 g), $^1$H NMR (CDCl$_3$) δ: 1.28 (3H, d), 2.09 (1H, m), 2.22 (1H, m), 2.43 (4H, t), 2.61 (1H, d), 2.80 (1H, m), 3.21 (1H, m), 3.46 (5H, m), 3.59 (1H, d), 3.94 (1H, d), 4.32 (1H, br), 5.14 (2H, s), 7.02 (1H, dd), 7.37 (5H, m), 7.74 (1H, d), 7.86 (2H, t), 8.28 (1H, d), 8.64 (1H, s), MS (ES): MH+ 500.

Description 46

Phenylmethyl (2S)-4-[(2'-{4-[(4-fluorophenyl)amino]-1-piperidinyl}-2,3'-bipyridin-5-yl)methyl]-2-methyl-1-piperazinecarboxylate (D46)

D45 (0.06 g, 0.12 mmol) and 4-fluoroaniline (0.013 g, 0.12 mmol) were dissolved in DCE. Molecular sieves (0.5 g) were added and the mixture was heated to 50° C. and stirred for 5 min. After this time, sodium triacetoxyborohydride was added and the mixture was stirred overnight, at 50° C. The sieves were filtered off and the filtrate was washed with saturated sodium bicarbonate solution. The organic layer was dried and concentrated to produce a yellow oil. Product purified by column chromatography, eluting 0-100% ethyl acetate/petrol to produce title compound as a colourless oil (0.029 g), $^1$H NMR (CDCl$_3$) δ: 1.25 (3H, d), 1.37 (2H, m), 1.66 (1H, br), 1.98 (2H, d), 2.10 (1H, m), 2.22 (1H, dd), 2.60 (1H, d), 2.82 (3H, m), 3.21 (1H, t), 3.32 (1H, m), 3.47 (3H, m), 3.54 (1H, d), 3.93 (1H, d), 4.31 (1H, br), 5.14 (2H, s), 6.52 (2H, m), 6.85 (2H, t), 6.97 (1H, m), 7.35 (5H, m), 7.72 (1H, d), 7.88 (2H, m), 8.27 (1H, d), 8.61 (1H, s), MS (ES): MH+ 595.

Description 47

Phenylmethyl 4-{[2'-(1,4-dioxa-8-azaspiro[4.5]dec-8-yl)-2,3'-bipyridin-5-yl]methyl}-1-piperazinecarboxylate (D47)

The title compound was prepared from D43 and phenylmethyl 1-piperazinecarboxylate using a method similar to that described for Description 44, MS (ES): MH+ 530.3

Description 48

Phenylmethyl 4-{[2'-(4-oxo-1-piperidinyl)-2,3'-bipyridin-5-yl]methyl}-1-piperazinecarboxylate (D48)

The title compound was prepared from D47 using a method similar to that of Description 45 except that the mixture was heated for 3.5 h, MS (ES): MH+ 486.2

Description 49

Phenylmethyl 4-[(2'-{4-[(4-fluorophenyl)amino]-1-piperidinyl}-2,3'-bipyridin-5-yl)methyl]-1-piperazinecarboxylate (D49)

The title compound was prepared from D48, 4-fluoroaniline and sodium cyanoborohydride using a method similar to that of Example 17 except that the mixture was stirred at rt overnight and purified by column chromatography (Horizon 25+M using 0-100% EtOAc/petrol then [10% MeOH/DCM in/DCM]) followed by MDAP, MS (ES): MH+ 581.3.

EXAMPLE 1

1-[3-(3-{[(3R,5S)-3,5-Dimethyl-1-piperazinyl]methyl}-1H-pyrazol-1-yl)-2-pyridinyl]-N-(4-fluorophenyl)-4-piperidinamine (E1)

D13 (0.56 g, 0.97 mmol) and potassium carbonate (1.13 g, 8.2 mml) were combined in MeOH (27 ml) and water (13.5 ml), then heated at 60° C. for 16 h. The solution was concentrated and the residue partitioned between 10% MeOH in DCM and water. The aqueous layer was re-extracted with 10% MeOH in DCM and the combined organic layers dried ($Na_2SO_4$) and concentrated to yield the title compound as a yellow foam (0.42 g). $\delta_H$ ($CDCl_3$) 1.01 (6H, d), 1.25-1.45 (3H, m), 1.69 (2H, d), 2.01 (2H, d), 2.77-2.84 (5H, m), 2.95 (2H, m), 3.26-3.40 (2H, br d), 3.43 (1H, br s), 3.64 (2H, s), 6.42 (1H, d), 6.52 (2H, m), 6.86 (2H, m), 6.65 (1H, m), 7.71 (1H, m), 7.93 (1H, d), 8.24 (1H, m). MS (ES): $MH^+$ 464.

EXAMPLE 1a

1-[3-(3{[(3R,5S)-3,5-dimethyl-1-piperazinyl]methyl}-1H-pyrazol-1-yl)-2-pyridinyl]-N-(4-fluorophenyl)-4-piperidinamine hydrochloride (E1a)

E1 (0.42 g, 0.91 mmol) was taken up in DCM (10 ml) and 1.2M HCl in diethylether (0.76 ml, 0.91 mmol) was added. Removal of the solvent in vacuo yielded the title compound as a yellow solid (0.45 g), $\delta_H$ (DMSO-$d_6$) 1.08 (6H, d), 1.83 (2H, d), 2.07 (2H, br t), 2.72 (2H, t), 2.95 (2H, br d), 3.16 (2H, d), 3.25 (3H, br s), 3.64 (2H, s), 5.38 (1H, br d), 6.45 (1H, s), 6.56 (2H, br s), 6.88 (2H, t), 7.03 (1H, m), 7.69 (1H, d), 8.12 (1H, s), 8.26 (2H, m), 9.09 (1H, br s).

Examples E2-E3 were prepared from the appropriate intermediates using methods similar to those described in Example 1.

EXAMPLE 4

1-[3-(5-{[(3R,5S)-3,5-Dimethyl-1-piperazinyl]methyl}-1,3-thiazol-2-yl)-2-pyridinyl]-N-(4-fluorophenyl)-4-piperidinamine (E4)

D18 (38 mg, 0.10 mmol), 4-fluoroaniline (10.9 mg, 0.1 mmol) and 3 Å molecular sieves (500 mg) in methanol (3 ml) were stirred at 25° C. for 16 h. Acetic acid (17 ul, 0.30 mmol) was added and the mixture stirred at 25° C. for 8 h. Sodium cyanoborohydride (9.3 mg, 0.15 mmol) was added and the mixture stirred at 25° C. for 48 h. After filtration, evaporation in vacuo gave a residue which was partitioned between DCM and 0.05M NaOH. The aqueous was extracted with DCM (×2) and evaporation of the combined organics gave a yellow oil. Purification by column chromatography on eluting with a 0-10% [MeOH/$NH_3$ (9:1)]/DCM gradient gave the title compound (27 mg). MS (ES): $MH^+$ 481.

EXAMPLE 4a

1-[3-(5-{[(3R,5S)-3,5-dimethyl-1-piperazinyl]methyl}-1,3-thiazol-2-yl)-2-pyridinyl]-N-(4-fluorophenyl)-4-piperidinamine dihydrochloride (E4a)

Treatment of E4 (27 mg) with 1M ethereal HCl afforded the title compound (16 mg). $\delta_H$ (DMSO-$d_6$) 1.31 (6H, br), 1.95 (2H, br d), 2.30 (2H, br), 2.89 (2H, t), 2.95-3.15 (2H, br), 3.29 (2H, br d), 3.50-4.30 (2H, overlapping signals), 7.30 (1H, m), 7.41 (2H, br), 7.55-7.77 (2H, br), 8.11 (1H, s), 8.41 (2H, m), 9.70 (1H, br s), 10.05 (1H, br s).

| Example No. | Structure | Compound Name | MH+ |
|---|---|---|---|
| E2 | 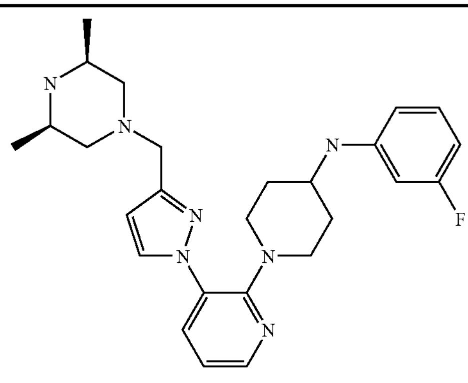 | 1-[3-(3-{[(3R,5S)-3,5-dimethyl-1-piperazinyl]methyl}-1H-pyrazol-1-yl)-2-pyridinyl]-N-(3-fluorophenyl)-4-piperidinamine | 464 |
| E3 | 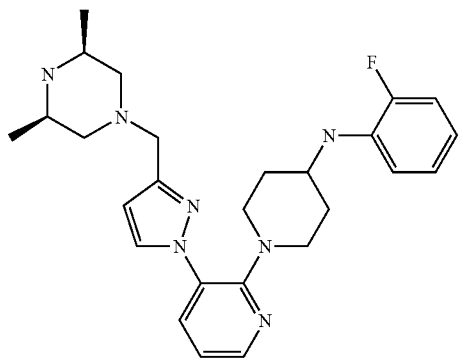 | 1-[3-(3-{[(3R,5S)-3,5-dimethyl-1-piperazinyl]methyl)-1H-pyrazol-1-yl)-2-pyridinyl]-N-(2-fluorophenyl)-4-piperidinamine | 464 |

EXAMPLE 5

1-[3-(5{[(3R,5S)-3,5-dimethyl-1-piperazinyl]methyl}-2-furanyl)-2-pyridinyl]-N-(4-fluorophenyl)-4-piperidinamine (E5)

D19 (85 mg, 0.23 mmol), (2R,6S)-2,6-dimethylpiperazine (26.5 mg, 0.23 mmol) in 1,2-dichloroethane (4 ml) were stirred at 25° C. for 16 h. Sodium (triacetoxy)borohydride (74.1 mg, 0.35 mmol) was added and the mixture stirred for 3 day. The mixture was washed with saturated $NaHCO_3$, water, dried ($Na_2SO_4$) and the solvent removed in vacuo. Purification by column chromatography on silica eluting with a 0-10% [MeOH/$NH_3$ (9:1)]/DCM gradient gave the title compound as an oily yellow solid (44 mg), $\delta_H$ (CDCl$_3$) 1.07 (6H, d), 1.55 (2H, m), 1.50-2.10 (6H, br), 2.12 (2H, m), 2.77-3.10 (4H, m), 3.40 (1H, m), 3.51 (2H, m), 3.61 (2H, s), 6.30 (1H, d), 6.55 (2H, dd), 6.80-6.99 (4H, m), 7.95 (1H, dd), 8.20 (1H, m). MS (ES): MH$^+$ 464.

EXAMPLE 6

1-[3-(5-{[(3R,5S)-3,5-Dimethyl-1-piperazinyl]methyl}-2-thienyl)-2-pyridinyl]-N-(4-fluorophenyl)-4-piperidinamine (E6)

D20 (78 mg, 0.2 mmol) and (2R,6S)-2,6-dimethylpiperazine (28 mg, 0.25 mmol) were dissolved in 1,2-dichloroethane (7 ml) and heated at 50° C. for 1.25 h. The reaction mixture was cooled to room temperature and sodium tri(acetoxy)borohydride (95 mg, 0.45 mmol) was added. The reaction mixture was stirred at room temp. under argon for 16 h. The mixture was diluted with DCM (8 ml) and washed with saturated NaHCO-$_3$ solution (10 ml). The organic layer was washed with a further portion of water (10 ml), then dried ($Na_2SO_4$) and concentrated. Purification by column chromatography on silica [0-10% (2M $NH_3$ in MeOH)/DCM gradient] gave the title compound as a foamy orange solid (41 mg) which was dissolved in methanol (1 ml). 1M HCl in ether (0.34 ml) was added and reaction mixture was concentrated to afford the di-HCl salt of the title compound as an orange solid (43 mg). $\delta_H$ (CDCl$_3$) 1.02 (6H, d), 1.60 (2H, m), 1.69 (2H, m), 2.06 (2H, m), 2.89 (6H, m), 3.36 (1H, m), 3.51 (2H, d), 3.71 (2H, s), 6.54 (2H, dd), 6.89 (4H, m), 7.18 (1H, d), 7.64 (1H, dd), 8.21 (1H, dd). MS (ES): MH$^+$ 480

EXAMPLE 7

1-[3-(4-{[(3R,5S)-3,5-Dimethyl-1-piperazinyl]methyl}-1,3-thiazol-2-yl)-2-pyridinyl]-N-(4-fluorophenyl)-4-piperidinamine dihydrochloride (E7)

D24 (40 mg, 0.1 mmol) and 4-fluoroaniline (11.6 mg, 0.1 mmol) were stirred in MeOH (6 ml) with 3 Å molecular sieves for 4 h. Acetic acid (25 mg, 0.415 mmol) was added and the mixture stirred for 16 h. Sodium tri(acetoxy)borohydride (9.8 mg, 0.15 mmol) was added and the mixture stirred for 24 h. Filtration, concentration and purification by column chromatography on silica [0-10% (2M $NH_3$ in MeOH)\DCM gradient] yielded the free base as a clear oil. The oil was taken up in DCM (5 ml) and excess 1M HCl in diethyl ether added. Concentration yielded the title compound as an off-white solid. $\delta_H$ (MeOH-d$_4$) 1.45 (6H, br s), 2.08 (2H, br s), 2.27 (2H, br s), 3.13 (2H, br s), 3.55 (2H, br s), 3.85 (5H, m), 4.69 (2H, br s), 7.37 (3H, m), 7.71 (2H, m), 8.07 (1H, br s), 8.39 (1H, br s), 8.60 (1H, br s). MS (ES): MH$^+$ 481.

Examples E8-E9 were prepared from the appropriate intermediates using methods similar to those described in Example 7.

| Example No. | Structure | Compound Name | MH+ |
|---|---|---|---|
| E8 | 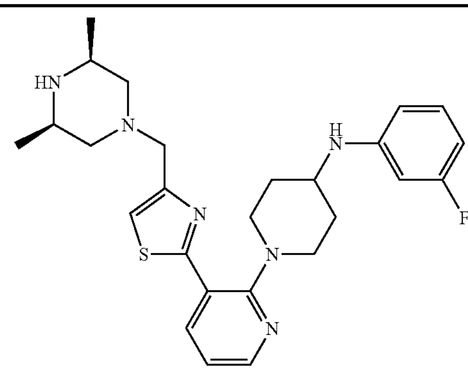 | 1-[3-(4-{[(3R,5S)-3,5-dimethyl-1-piperazinyl]methyl}-1,3-thiazol-2-yl)-2-pyridinyl]-N-(3-fluorophenyl)-4-piperidinamine | 481 |
| E9 | 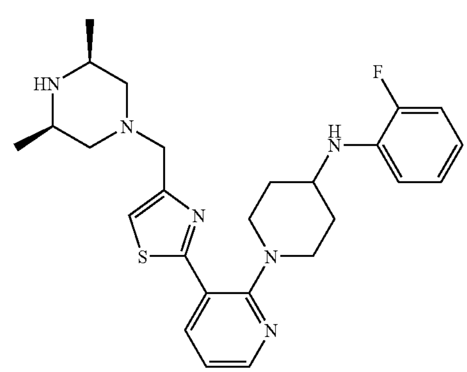 | 1-[3-(4-{[(3R,5S)-3,5-dimethyl-1-piperazinyl]methyl}-1,3-thiazol-2-yl)-2-pyridinyl]-N-(2-fluorophenyl)-4-piperidinamine | 481 |

EXAMPLE 10

1-(5-{[(3R,5S)-3,5-Dimethyl-1-piperazinyl]methyl}-2,3'-bipyridin-2'-yl)-N-(4-fluorophenyl)-4-piperidinamine (E10)

D28 (0.1 g, 0.26 mmol) and 4-fluoroaniline (0.029 g, 0.026 mmol) were dissolved in MeOH (5 ml) with molecular sieves (0.5 g) and stirred at room temp. for 4 h. Acetic acid (0.047 g, 0.79 mmol) was added and the mixture stirred for 24 h. Sodium cyanoborohydride (0.025 g, 0.40 mmol) was added and the mixture was stirred at room temp. for a further 24 h. The mixture was filtered to remove the molecular sieves and the filtrate concentrated in vacuo. Purification by column chromatography on silica [0-10% (2M $NH_3$ in MeOH)/DCM gradient] followed mass-directed auto-purification gave the title compound as a yellow solid (0.025 g). $\delta_H$ ($CDCl_3$) 1.01 (6H, d), 1.36 (2H, m), 1.66 (2H, t), 1.97 (2H, d), 2.74 (2H, m), 2.90 (4H, m), 3.31 (1H, m), 3.50 (4H, m), 6.51 (2H, m), 6.85 (2H, t), 6.96 (1H, m), 7.69 (1H, d), 7.85 (2H, m), 8.27 (1H, m), 8.60 (1H, s). MS (ES): $MH^+$ 475.

EXAMPLE 10a 1-(5{[(3R,5S)-3,5-Dimethyl-1-piperazinyl]methyl}-2,3'-bipyridin-2'-yl)-N-(4-fluorophenyl)-4-piperidinamine hydrochloride (E10a)

E10 (0.025 g) was dissolved in DCM (1 ml) and 1.2M HCl in diethyl ether (0.045 ml) was added. The mixture was concentrated to produce the title compound as a white solid (0.022 g). $\delta_H$ (DMSO-$d_6$) 1.15 (6H, d), 1.31 (2H, m), 1.81 (2H, d), 2.04 (2H, t), 2.78 (2H, t), 2.90 (2H, d), 3.37 (5H, m), 3.63 (2H, s), 5.37 (1H, d, NH), 6.54 (2H, m), 6.89 (2H, t), 7.01 (1H, m), 7.76 (1H, d), 7.81 (1H, d), 7.88 (1H, d), 8.24 (1H, m), 8.37 (1H, br d), 8.61 (1H, s), 9.12 (1H, br d). MS (ES): $MH^+$ 475.

EXAMPLE 11

N-(4-Fluorophenyl)-1-[3-(3{[(3S)-3-methyl-1-piperazinyl]methyl}-1H-pyrazol-1-yl)-2-pyridinyl]-4-piperidinamine (E11)

D33 (200 mg, 0.64 mmol), bromopyridine D10 (186 mg, 0.53 mmol), copper(I)iodide (5 mg, 0.03 mmol), potassium carbonate (88 mg, 0.64 mmol) and L-proline (8 mg, 0.064 mmol) were combined in DMSO (1 ml) and heated at 170° C. in a microwave reactor for 12 h. The reaction mixture was partitioned between DCM and water and the organic layers separated (×3), dried ($Na_2SO_4$) and concentrated to give a crude brown oil (325 mg). This oil was chromatographed (Biotage Horizon 40+S, eluting with 0 to 10% ethyl acetate/pet ether). Combination of appropriate fractions gave a colourless oil (102 mg). Methanol (15 ml) was added along with Pd black (40 mg) and the material hydrogenated at room temperature. LCMS showed the reaction complete by 3 h, the Pd was filtered off and the reaction mixture was concentrated to give a colourless oil (85 mg). Chromatography (Biotage Horizon 12+M, eluting with 0-10% MeOH/$NH_3$/DCM followed by 10-20% MeOH/$NH_3$/DCM) yielded the title compound as a colourless oil (61 mg). $\delta_H$ ($CDCl_3$, 400 MHz): 1.03 (3H, d), 1.40 (2H, m), 1.79 (1H, t), 2.01 (4H, br d), 2.14 (1H, m), 2.77-2.84 (4H, m), 2.95 (3H, m), 3.28 (3H, br d), 3.65 (2H, s), 6.41 (1H, d), 6.53 (2H, m), 6.87 (2H, m), 6.95 (1H, m), 7.72 (1H, dd), 7.95 (1H, d), 8.23 (1H, m). MS (ES): $MH^+$ 450

Treatment of the above with 1.2M HCl in ether (0.11 ml) formed the monohydrochloride salt of the title compound as a white solid (50 mg).

EXAMPLE 12

(3R,5S)-1-{[1-(2-{4-[(4-Fluorophenyl)oxy]-1-piperidinyl}-3-pyridinyl)-1H-pyrazol-3-yl]methyl}-3,5-dimethylpiperazine (E12)

D38 (24 mg, 0.043 mmol) and KOH (24 mg, 0.42 mmol) were combined in isopropanol and heated to 100° C. for 4 h. The solvent was removed and the residues partitioned between 10% MeOH/DCM and water. The aqueous was re-extracted with 10% MeOH/DCM. The combined organics were combined, dried and concentrated to yield the product as a yellow oil, $\delta_H$ ($CDCl_3$, 400 MHz): 1.01-1.02 (6H, d), 1.55 (1 h, bs), 1.68-1.79 (4H, m), 1.93-1.98 (2H, m), 2.82-2.98 (6H, m), 3.23-3.29 (2H, m), 3.65 (2H, s), 4.27-4.31 (1H, m), 6.42-6.43 (1H, d), 6.82-6.86 (2H, m), 6.92-7.00 (3H, m), 7.71-7.74 (1H, dd), 7.95 (1H, d), 8.23-8.25 (1H, m), MS (ES): $MH^+$ 465.2

This yellow oil was treated with 1.1 eq of 1M HCl in $Et_2O$ to give the hydrochloride salt of the title compound (6.2 mg), MS (ES): $MH^+$ 465.3

EXAMPLE 13

(3R,5S)-1-{[1-(2-{4-[(2-Fluorophenyl)oxy]-1-piperidinyl}-3-pyridinyl)-1H-pyrazol-3-yl]methyl}-3,5-dimethylpiperazine (E13)

The title compound was prepared using a method similar to that described for E12 using D39, MS (ES): $MH^+$ 465.3

EXAMPLE 14

(3R,5S)-1-{[1-(2-{4-[(3-Fluorophenyl)oxy]-1-piperidinyl}-3-pyridinyl)-1H-pyrazol-3-yl]methyl}-3,5-dimethylpiperazine (E14)

The title compound was prepared using a method similar to that described for E12 using D40, MS (ES): $MH^+$ 465.3

EXAMPLE 15

(3S)-1-{[1-(2-{4-[(3-Fluorophenyl)oxy]-1-piperidinyl}-3-pyridinyl)-1H-pyrazol-3-yl]methyl}-3-methylpiperazine (E15)

D41 (51 mg, 0.0.87 mmol) and palladium black (19 mg) were combined in MeOH (5 ml) and hydrogenated at atmospheric pressure for 3 h. The mixture was filtered through Celite and the filtrate concentrated to yield the product as an off-white oil. $\delta_H$ ($CDCl_3$, 400 MHz): 1.23-1.26 (3H, d), 1.72-1.81 (2H, m), 1.97-2.02+(3H, m), 2.29-2.34 (1H, m), 2.87-2.92 (4H, m), 2.96-3.12 (3H, m), 3.24-3.29 (2H, m), 3.67 (2H, s), 4.20 (1H, bs), 4.36-4.39 (1H, m), 6.41-6.42 (1H, d), 6.59-6.68 (3H, m), 6.94-6.97 (1H, m), 7.17-7.22 (1H, m), 7.72-7.74 (1 h, dd), 7.97-7.98 (1H, d), 8.24-8.25 (1H, m), MS (ES): $MH^+$ 451.3

This whole was treated with 1.1 eq of 1M HCl in $Et_2O$ to give the hydrochloride salt of the title compound (39.8 mg), MS (ES): $MH^+$ 451.3

EXAMPLE 16

(3S)-1-{[1-(2-{4-[4-Fluorophenyl)oxy]-1-piperidinyl}-3-pyridinyl)-1H-pyrazol-3-yl]methyl}-3-methylpiperazine monohydrochloride (E16)

The title compound was prepared from D42 using a method similar to that described for E15, MS (ES): MH+ 451.3

EXAMPLE 17

1-(5{[(3R,5S)-3,5-Dimethyl-1-piperazinyl]methyl}-2,3'-bipyridin-2'-yl)-N-(3-fluorophenyl)-4-piperidinamine (E17)

D28 (0.115 g, 0.3 mmol) and 3-fluoroaniline (0.034 g, 0.3 mmol) were dissolved in methanol with added molecular sieves (0.5 g). The mixture was allowed to stir for 2 h at rt. Acetic acid (0.055 g, 0.91 mmol) was added and the mixture was stirred overnight at rt. Sodium cyanoborohydride (0.029 g, 0.46 mmol) was added and the mixture was allowed to stir at rt over the weekend. The sieves were filtered off and the solvent removed under vacuum. The residue was taken up in DCM and washed with saturated sodium bicarbonate solution. The organic layer was dried and concentrated to produce a yellow oil. Product purified by MDAP to produce title compound as a colourless oil (0.042 g), $^1$H NMR (CDCl$_3$) δ: 1.02 (6H, d), 1.38 (2H, m), 1.66 (2H, t), 1.98 (2H, d), 2.75 (2H, d), 2.94 (4H, m), 3.36 (1H, br), 3.49 (2H, d), 3.53 (2H, s), 3.66 (1H, br), 6.25 (1H, d), 6.33 (2H, m), 6.97 (1H, dd), 7.05 (1H, dd), 7.69 (1H, d), 7.85 (2H, m), 8.27 (1H, dd), 8.61 (1H, s), MS (ES): MH+ 475.

The above was combined with 1.2M HCl in diethyl ether (0.074 ml) to produce mono HCl salt (0.043 g), MS (ES): MH+ 475.

EXAMPLE 18

N-(4-Fluorophenyl)-1-(5-{[(3S)-3-methyl-1-piperazinyl]methyl}-2,3'-bipyridin-2'-yl)-4-piperidinamine (E18)

D46 (0.029 g, 0.049 mmol) was combined with palladium black (0.015 g) in methanol (4 ml) and stirred under a hydrogen atmosphere for 4 h. The catalyst was removed by filtration through Celite and the solvent removed under vacuum to produce crude product as colourless oil. Product purified by MDAP to produce title compound as colourless oil (0.014 g), $^1$H NMR (CDCl$_3$) δ: 1.00 (3H, d), 1.36 (2H, dd), 1.72 (1H, t), 1.97 (2H, d), 2.07 (1H, m), 2.75 (2H, d), 2.90 (5H, m), 3.34 (1H, m), 3.52 (4H, m), 6.51 (2H, m), 6.85 (2H, t), 6.96 (1H, dd), 7.70 (1H, dd), 7.85 (2H, t), 8.27 (1H, d), 8.61 (1H, s), MS (ES): MH+ 461.

The above was dissolved in DCM and 1.2M HCl in diethyl ether (0.025 ml) added. Solvent removed to produce mono HCl salt (0.011 g), MS (ES): MH+ 461.

EXAMPLE 19

N-(4-Fluorophenyl)-1-[5-(1-piperazinylmethyl)-2,3'-bipyridin-2'-yl]-4-piperidinamine hydrochloride (E19)

The title compound was prepared from D49 using a method similar to that of Example 18, except that the product was purified by column chromatography on Horizon 12+M using 0-100% (10% NH$_3$/MeOH in DCM)/DCM, MS (ES): MH+ 447.2

Compounds of the invention may be tested for in vitro biological activity in accordance with the following FLIPR and GTPγS assays:

GPR38 FLIPR Functional Agonist Assay Protocol

HEK-293 cells stably expressing the GPR38 receptor were seeded (10,000 cells/well) into poly-D-lysine coated 384-well black-wall, clear-bottom microtitre plates (Becton Dickinson) 24 h prior to assay. On day of assay, cells were washed (×2) with 80 ul of assay buffer (Hanks Balanced Salts Solution (HBSS), 10 mM HEPES, 200 μM Ca$^{2+}$, 2.5 mM probenecid) using the EMBLA cell washer. After the final wash, buffer was aspirated to leave a residual volume of 30 ul on the cells. Cells were loaded with 1 μM (final) Fluo-4-AM fluorescent indicator dye (TefLabs) in assay buffer, (20 ul loading solution added to each well using the Multidrop). Plates were incubated for 1 h at 37° C., before being washed (×3) with 80 ul assay buffer using the EMBLA cell washer; 30 ul residual being left after the final wash. Plates were then assayed on a Fluorometric Imaging Plate Reader (FLIPR, Molecular Devices). Test compounds were prepared in assay buffer without probenecid, but containing 0.03% CHAPS. In the FLIPR, 10 ul of test compound was added to the cells and changes in fluorescence measured over a 2 min timeframe. Maximum change in fluorescence over baseline was used to determine agonist response and concentration response curves were constructed, using a 4-parameter logistic equation.

The following alternative procedure may also be used:

HEK-293 cells stably expressing the GPR38 receptor were seeded (30,000 cells/100 ul growth media/well) into poly-D-lysine coated 96-well black-wall, clear-bottom microtitre plates (Corning) 24 hours prior to assay. On the day of assay the cells were loaded with 2 μM (final) Fluo-4-AM fluorescent indicator dye (Molecular Probes) and 1 mM (final) probenicid in assay buffer (145 mM sodium chloride, 2.5 mM potassium chloride, 10 mM Hepes, 10 mM glucose, 1.2 mM magnesium chloride, 1.5 mM calcium chloride and 0.1% BSA) (50 ul loading solution added to each well). Plates were incubated for 1 hour at 25° C., before being washed 4 times with 100 ul assay buffer using the EMBLA cell washer; 150 ul residual being left after the final wash. The cells were then incubated at 25° C. for 20 minutes and the plates were then assayed on a Fluorometric Imaging Plate Reader (FLIPR, Molecular Devices). Test compounds were prepared in assay buffer without probenecid. In the FLIPR, 50 ul of test compound was added to the cells and changes in fluorescence measured over a 2 minute timeframe. Maximum change in fluorescence over baseline was used to determine agonist response and concentration response curves were constructed, using a 4-parameter logistic equation.

Compounds of the invention which have been tested have a pEC50>5.0 in the FLIPR assay, more preferably >5.5, for example >6.0.

GPR38 GTPγS Functional Agonist Assay Protocol

For each compound being assayed, in an Opti clear bottom 96 well plate, is added:—

(a) 20 μl of test compound (or 10 μl of guanosine 5'-triphosphate (GTP) as non-specific binding control) diluted to required concentration in assay buffer (20 mM N-2-Hydroxyethylpiperazine-N'-2-ethanesulfonic acid (HEPES)+100 mM NaCl+10 mM MgCl$_2$, pH adjusted to 7.4 with NaOH);

(b) 60 μl bead/membrane/GDP mix prepared by suspending wheat germ agglutinin-polyvinyltoluene (WGA-PVT) scintillation proximity assay (SPA) beads at 100 mg/ml in assay buffer followed by mixing with membrane (prepared in accordance with the methodology described above) and diluting in assay buffer to give a final volume of 60 μl which contains 10 μg protein and 0.5 mg bead per well—mixture is pre-mixed at 4° C. for 30 min on a roller and just prior to addition to the plate, 10 μM final concentration of guanosine 5' diphosphate (GDP—diluted in assay buffer) is added;
(c) 20 μl guanosine 5' [γ35-S] thiotriphosphate, triethylamine salt (Amersham; radioactivity concentration=37 kBq/μl or 1 mCi/ml; Specific Activity 1160 Ci/mmol) diluted to 1.9 nM in assay buffer to give 0.38 nM final.

The plate is incubated on a shaker at 25° C. for 30 min followed by centrifugation for 5 min at 1500 rpm. The plate is read between 3 and 6 h after completion of centrifuge run in a Wallac Microbeta counter on a 1 min normalised tritium count protocol. Data is analysed using a 4-parameter logistic equation. Basal activity used as minimum.

The following alternative procedure may also be used:
Membranes are derived from bulk cell cultures of HEK293 cell lines transiently transfected with hGPR38R and Go G-protein. P2 membranes fractions are prepared, aliquoted and stored at −80° C.

For each compound being assayed, the following is added into a white Greiner 384 well plate:—
(a) 1 μl of test compound diluted to required concentration in DMSO.
(b) 20 μl bead/membrane/Saponin/GDP mix prepared as follows; —suspension of LEADseeker wheat germ agglutinin (WGA) scintillation proximity assay (SPA) beads at 25 mg/ml in assay buffer (20 mM N-2-Hydroxyethylpiperazine-N'-2-ethanesulfonic acid (HEPES)+100 mM NaCl+10 mM $MgCl_2$, pH adjusted to 7.4 with KOH containing saponin at 150 ug/ml. Mixing of bead suspension with membranes at 500 ug/ml (prepared in accordance with the methodology described above) and diluting in assay buffer to give a final volume of 20 μl which contains 5 μg protein and 0.25 mg bead per well.

Mixture is pre-mixed for 30 minutes on a roller and just prior to addition to the plate, 3 μM final assay concentration of guanosine 5' diphosphate (GDP) (diluted in assay buffer) is added.
(c) 25 μl guanosine 5' [γ35-S] thiotriphosphate, triethylamine salt (Amersham; radioactivity concentration=37 kBq/μl or 1 mCi/ml; Specific Activity 1160 Ci/mmol) diluted to 0.6 nM in assay buffer to give 0.33 nM final assay concentration.

The plate is then spun for 2 minutes at 1500 rpm and then incubated at room temperature for 4 hours. The plate is then read on a Viewlux Plux (Perkin Elmer). Data is analysed using a 4-parameter logistic equation.

Preferred compounds of the invention have a pEC50>5.0 in the GTPγS assay, more preferably >−5.5.

What is claimed is:
1. A compound of formula (I),

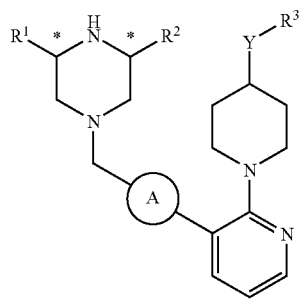

(I)

wherein:
A is a 5 or 6 membered heteroaryl ring, optionally substituted with 1, 2 or 3 groups independently selected from halogen, $C_{(1-4)}$ alkyl and $C_{(1-4)}$ alkoxy;
$R^1$ and $R^2$ are independently selected from H and $C_{(1-4)}$ alkyl;
Y is selected from NH, O and $CH_2$;
$R^3$ is an optionally substituted phenyl, wherein when $R^3$ is a substituted phenyl, said substituted phenyl has 1, 2 or 3 substituents, each independently selected from halogen, $C_{(1-4)}$alkyl, $C_{(1-4)}$alkoxy, $C_{(3-7)}$cycloalkyl, hydroxy, trifluoromethoxy, trifluoromethyl, nitro, cyano, phenyl, $NH_2$, $NHR^4$, $NR^4R^5$, $NHCOR^4$, $NHSO_2R^4$, $C(O)CF_3$, $C(O)C_{(1-4)}$alkyl, $C(O)C_{(3-7)}$cycloalkyl, $C(O)OC_{(1-4)}$alkyl, $C(O)OC_{(3-7)}$cycloalkyl, $OC(O)C_{(1-4)}$alkyl, $OC(O)C_{(3-7)}$cycloalkyl, $CONH_2$, $CONHR^4$, $CONR^4R^5$, $SOR^5$, $SO_2R^5$, $OSO_2R^5$, $OSO_2CF_3$, $SO_2NH_2$, $SO_2NHR^4$ and $SO_2NR^4R^5$;
wherein $R^4$ and $R^5$ may be the same or different and are independently selected from $C_{(1-4)}$ alkyl, phenyl optionally substituted with halogen, and 5 or 6 membered heteroaryl optionally substituted with halogen;
or a pharmaceutically acceptable salt thereof.

2. The compound or salt according to claim 1, wherein A is selected from pyrazolyl, thiazolyl, furanyl, thienyl and pyridyl.

3. The compound or salt according to claim 1, wherein $R^3$ is substituted by 1, 2 or 3 groups selected from halogen, cyano, $C_{(1-4)}$alkyl, $C_{(1-4)}$alkoxy, $C_{(3-7)}$cycloalkyl, trifluoromethoxy and trifluoromethyl.

4. The compound or salt according to claim 1, wherein Y is NH.

5. A compound selected from:
1-[3-(3-{[(3R,5S)-3,5-Dimethyl-1-piperazinyl]methyl}-1H-pyrazol-1-yl)-2-pyridinyl]-N-(4-fluorophenyl)-4-piperidinamine;
1-[3-(3-{[(3R,5S)-3,5-dimethyl-1-piperazinyl]methyl}-1H-pyrazol-1-yl)-2-pyridinyl]-N-(3-fluorophenyl)-4-piperidinamine;
1-[3-(3-{[(3R,5S)-3,5-dimethyl-1-piperazinyl]methyl}-1H-pyrazol-1-yl)-2-pyridinyl]-N-(2-fluorophenyl)-4-piperidinamine;
1-[3-(5-{[(3R,5S)-3,5-Dimethyl-1-piperazinyl]methyl}-1,3-thiazol-2-yl)-2-pyridinyl]-N-(4-fluorophenyl)-4-piperidinamine;
1-[3-(5-{[(3R,5S)-3,5-dimethyl-1-piperazinyl]methyl}-2-furanyl)-2-pyridinyl]-N-(4-fluorophenyl)-4-piperidinamine;
1-[3-(5-{[(3R,5S)-3,5-Dimethyl-1-piperazinyl]methyl}-2-thienyl)-2-pyridinyl]-N-(4-fluorophenyl)-4-piperidinamine;
1-[3-(4-{[(3R,5S)-3,5-Dimethyl-1-piperazinyl]methyl}-1,3-thiazol-2-yl)-2-pyridinyl]-N-(4-fluorophenyl)-4-piperidinamine dihydrochloride;
1-[3-(4-{[(3R,5S)-3,5-dimethyl-1-piperazinyl]methyl}-1,3-thiazol-2-yl)-2-pyridinyl]-N-(3-fluorophenyl)-4-piperidinamine;
1-[3-(4-{[(3R,5S)-3,5-dimethyl-1-piperazinyl]methyl}-1,3-thiazol-2-yl)-2-pyridinyl]-N-(2-fluorophenyl)-4-piperidinamine;
1-(5-{[(3R,5S)-3,5-Dimethyl-1-piperazinyl]methyl}-2,3'-bipyridin-2'-yl)-N-(4-fluorophenyl)-4-piperidinamine;
N-(4-Fluorophenyl)-1-[3-(3-{[(3S)-3-methyl-1-piperazinyl]methyl}-1H-pyrazol-1-yl)-2-pyridinyl]-4-piperidinamine;

(3R,5S)-1-{[1-(2-{4-[(4-Fluorophenyl)oxy]-1-piperidinyl}-3-pyridinyl)-1H-pyrazol-3-yl]methyl}-3,5-dimethylpiperazine;

(3R,5S)-1-{[1-(2-{4-[(2-Fluorophenyl)oxy]-1-piperidinyl}-3-pyridinyl)-1H-pyrazol-3-yl]methyl}-3,5-dimethylpiperazine;

(3R,5S)-1-{[1-(2-{4-[(3-Fluorophenyl)oxy]-1-piperidinyl}-3-pyridinyl)-1H-pyrazol-3-yl]methyl}-3,5-dimethylpiperazine;

(3S)-1-{[1-(2-{4-[(3-Fluorophenyl)oxy]-1-piperidinyl}-3-pyridinyl)-1H-pyrazol-3-yl]methyl}-3-methylpiperazine;

(3S)-1-{[1-(2-{-4-[4-Fluorophenyl)oxy]-1-piperidinyl}-3-pyridinyl)-1H-pyrazol-3-yl]methyl}-3-methylpiperazine monohydrochloride;

1-(5-{[(3R,5S)-3,5-Dimethyl-1-piperazinyl]methyl}-2,3'-bipyridin-2'-yl)-N-(3-fluorophenyl)-4-piperidinamine;

N-(4-Fluorophenyl)-1-(5-{[(3S)-3-methyl-1-piperazinyl]methyl}-2,3'-bipyridin-2'-yl)-4-piperidinamine; and N-(4-Fluorophenyl)-1-[5-(1-piperazinylmethyl)-2,3'-bipyridin-2'-yl]-4-piperidinamine hydrochloride.

6. A pharmaceutical composition comprising the compound or salt according to claim 1 and a pharmaceutically acceptable carrier.

7. A method of treatment of a condition in a human which can be mediated via the GPR38 receptor which comprises administering a therapeutically effective amount of the compound or salt according to claim 1 to said human, wherein said condition is selected from intestinal pseudo-obstruction, paralytic ileus following surgery or other manipulation, gastric stasis or hypomotility caused by diabetes and/or by the administration of other drugs, Crohn's disease, and colitis.

8. A process for the preparation of the compound of formula (I) or salt thereof, according to claim 1, which process comprises reacting a compound of formula (II),

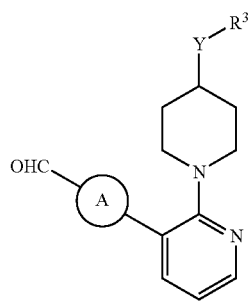

(II)

wherein A, Y and $R^3$ are as defined in claim 1, with an appropriately substituted piperazine (III),

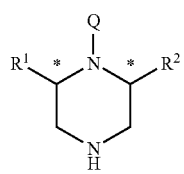

(III)

wherein $R^1$ and $R^2$ are as defined in claim 1 and Q is hydrogen or a suitable nitrogen protecting group, in reaction conditions suitable for a reductive alkylation, in a suitable solvent, and thereafter optionally carrying out one or both of the following reactions:
1. removing any protecting group;
2. forming a suitable pharmaceutical acceptable salt of the compound so formed.

9. A process for the preparation the compound of formula (I) or salt thereof, according to claim 1, wherein A is pyrazolyl, which process comprises reacting a compound of formula (VIII),

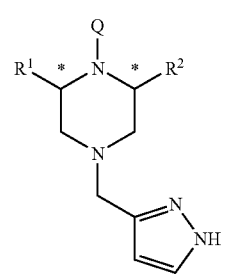

(VIII)

wherein $R^1$ and $R^2$ are as defined in claim 1 and Q is hydrogen or a suitable nitrogen protecting group, with a compound of formula (IV),

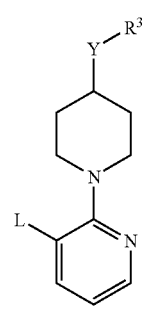

(IV)

wherein Y and $R^3$ are as defined in claim 1 and L is a leaving group, in the presence of a suitable base, in the presence of a suitable catalyst in a suitable solvent;

and thereafter optionally carrying out one or both of the following reactions:
1. removing any protecting group;
2. forming a suitable pharmaceutical acceptable salt of the compound so formed.

10. A process for the preparation of the compound of formula (I) or salt thereof, according to claim 1, which process comprises reacting a compound of formula (XI),

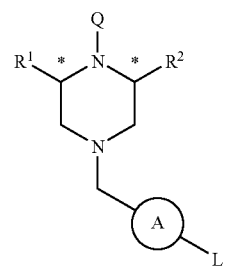

(XI)

wherein A, $R^1$ and $R^2$ are as defined in claim 1, L is a leaving group and Q is hydrogen or a suitable nitrogen protecting group, with a compound of formula (XII),

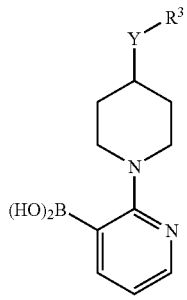

(XII)

wherein Y and $R^3$ are as defined in claim 1, in the presence of a suitable base, in the presence of suitable catalyst, in a suitable solvent;

and thereafter optionally carrying out one or both of the following reactions:
1. removing any protecting group;
2. forming a suitable pharmaceutical acceptable salt of the compound so formed.

11. A process for the preparation of the compound of formula (I) or salt thereof according to claim 1, wherein Y is NH, which process comprises reacting a compound of formula (XIII),

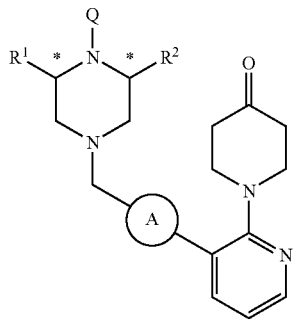

(XIII)

wherein A, $R^1$ and $R^2$ are as defined in claim 4 and Q is hydrogen or a suitable nitrogen protecting group, with a suitable aniline having the formula $R^3NH_2$, wherein $R^3$ is as defined in claim 1, under reaction conditions suitable for a reductive alkylation, in the presence of an acid, in the presence of molecular sieves and in a suitable solvent;

and thereafter optionally carrying out one or both of the following reactions:
1. removing any protecting group;
2. forming a suitable pharmaceutical acceptable salt of the compound so formed.

* * * * *